(12) United States Patent
Stetten et al.

(10) Patent No.: US 7,559,895 B2
(45) Date of Patent: **\*Jul. 14, 2009**

(54) COMBINING TOMOGRAPHIC IMAGES IN SITU WITH DIRECT VISION USING A HOLOGRAPHIC OPTICAL ELEMENT

(75) Inventors: George DeWitt Stetten, Pittsburgh, PA (US); Andreas G. Nowatzyk, San Jose, CA (US)

(73) Assignee: University of Pittsburgh-Of The Commonwealth System Of Higher Education, Pittsburgh, PA (US)

( \* ) Notice: Subject to any disclaimer, the term of this patent is extended or adjusted under 35 U.S.C. 154(b) by 1141 days.

This patent is subject to a terminal disclaimer.

(21) Appl. No.: 10/126,453

(22) Filed: Apr. 19, 2002

(65) Prior Publication Data

US 2003/0199765 A1    Oct. 23, 2003

Related U.S. Application Data

(63) Continuation-in-part of application No. 09/686,677, filed on Oct. 11, 2000.

(60) Provisional application No. 60/216,860, filed on Jul. 7, 2000.

(51) Int. Cl.
*A61B 8/00* (2006.01)
(52) U.S. Cl. ....................................... 600/443
(58) Field of Classification Search .............. 600/407, 600/424, 425, 427, 443, 444; 128/916
See application file for complete search history.

(56) References Cited

U.S. PATENT DOCUMENTS

| | | | |
|---|---|---|---|
| 5,261,404 A \* | 11/1993 | Mick et al. | 600/425 |
| 5,335,260 A | 8/1994 | Arnold | |
| 5,526,812 A \* | 6/1996 | Dumoulin et al. | 600/407 |
| 5,823,958 A \* | 10/1998 | Truppe | 600/426 |
| 5,896,226 A | 4/1999 | Peuchot et al. | |
| 5,898,503 A | 4/1999 | Keller et al. | |
| 6,178,340 B1 \* | 1/2001 | Svetliza | 600/310 |
| 6,216,029 B1 \* | 4/2001 | Paltieli | 600/427 |
| 6,447,451 B1 \* | 9/2002 | Wing et al. | 600/437 |
| 6,490,477 B1 \* | 12/2002 | Zylka et al. | 600/429 |
| 6,599,247 B1 \* | 7/2003 | Stetten | 600/443 |
| 2002/0120424 A1 | 8/2002 | Hauger et al. | |
| 2005/0101868 A1 | 5/2005 | Ridley et al. | |
| 2006/0257009 A1 | 11/2006 | Wang et al. | |

\* cited by examiner

*Primary Examiner*—Eric F Winakur
*Assistant Examiner*—Michael T Rozanski
(74) *Attorney, Agent, or Firm*—Reed Smith LLP

(57) ABSTRACT

A device for combining tomographic images with human vision using a half-silvered mirror to merge the visual outer surface of an object (or a robotic mock effector) with a simultaneous reflection of a tomographic image from the interior of the object. The device maybe used with various types of image modalities including ultrasound, CT, and MRI. The image capture device and the display may or may not be fixed to the semi-transparent mirror. If not fixed, the imaging device may provide a compensation device that adjusts the reflection of the displayed ultrasound on the half-silvered mirror to account for any change in the image capture device orientation or location.

37 Claims, 14 Drawing Sheets

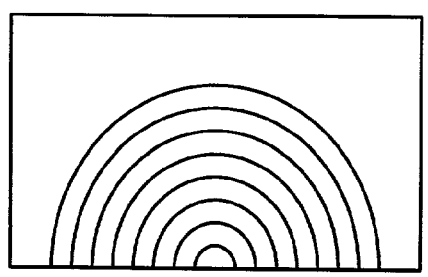
H.O.E. "Zone Plate"
FIGURE 14A
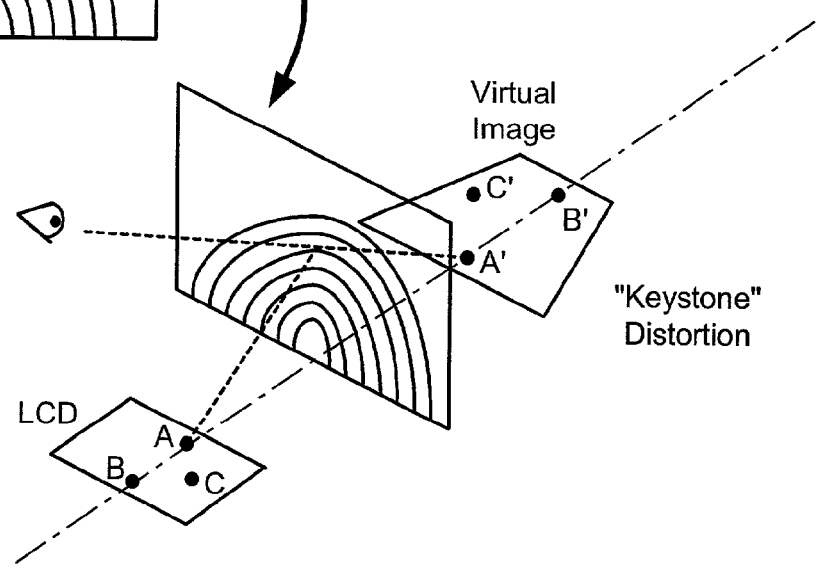
FIGURE 14B
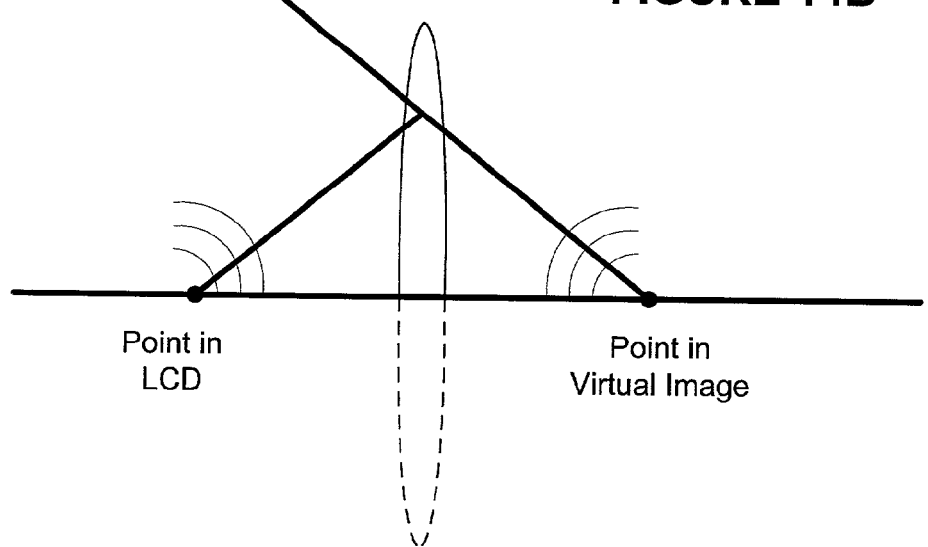

COMBINING TOMOGRAPHIC IMAGES IN SITU WITH DIRECT VISION USING A HOLOGRAPHIC OPTICAL ELEMENT

RELATED APPLICATION DATA

This application claims the benefit and is a CIP of application Ser. No. 09/686,677, filed Oct. 11, 2000, and claims the benefit of provisional application Ser. No. 60/216,860 filed Jul. 7, 2000.

BACKGROUND OF THE INVENTION

1. Field of the Invention

The present invention generally relates to image display devices and methods therefor, and, more particularly, the present invention relates to methods and devices for combining a reflection of a tomographic image with human vision during subcutaneous medical procedures.

2. Description of the Background

Because human vision depends at least partially on the detection of reflected visible light, humans cannot "see" into objects through which light does not pass. In other words, humans cannot see into the interior sections of a non-transparent, solid object. Quite often, and in many different technology areas, this sight limitation may impede or hinder the effective completion of a particular task. Various partial solutions to this problem have been utilized in the past (miniature cameras, x-ray methodologies, etc.). However, there is a continued need for improvement to the methods by which the interior of an object is displayed, especially using a real-time imaging modality.

Perhaps in no other field is this sight limitation more of a hindrance than in the medical field. Clinical medicine often calls for invasive procedures that commence at the patient's skin and proceed inward to significant depths within the body. For example, biopsy needles introduced through the abdominal wall to take samples of liver tissue for diagnosis of cancer must pass through many centimeters of intervening tissue. One potential problem with such procedures is the lack of real-time visual feedback in the vicinity of critical structures such as the hepatic arteries.

Standard imaging modalities such as Computerized Tomography (CT) and Magnetic Resonance Imaging (MRI) can provide data for stereotactic registration of biopsy needles within targets in the liver, lungs, or elsewhere, but these methods are typically characterized by the physical displacement of the patient between the time of image acquisition and the invasive procedure. Real-time imaging modalities offer more immediate feedback. Among such real-time modalities, ultrasound may be well-suited for guidance of needles because it preferably is relatively portable, is inexpensive, produces no ionizing radiation, and displays a tomographical slice, as opposed to angiography, which displays a projection. Compared with angiography, ultrasound may offer the additional advantage that clinicians are not rushed through procedures by a desire to keep exposure times to a minimum.

Conventional two dimensional (2D) ultrasound is routinely used to guide liver biopsies, with the needle held in a "guide" attached to a transducer. The guide keeps the biopsy needle in the plane of the image while the tip of the needle is directed to targets within that same plane. This system typically requires a clinician to look away from his hands at a video monitor, resulting in a loss of direct hand-eye coordination. Although the clinician can learn this less direct form of coordination, the natural instinct and experience of seeing one's hands before one's eyes is preferred.

As a further disadvantage, the needle-guide system constrains the biopsy needle to lie in the image plane, whereas the clinician may prefer the needle to intersect the image plane during some invasive procedures. For example, when inserting an intravenous (IV) catheter into an artery, the optimal configuration may be to use the ultrasound image to visualize the artery in cross-section while inserting the needle roughly perpendicular to the image into the lumen of the artery. The prior art system just described may not be capable of accomplishing this task.

A related visualization technology has been developed where three dimensional (3D) graphical renderings of previously obtained CT data are merged with an observer's view of the patient using a partial or semi-transparent mirror, also known as a "half-silvered" mirror. A partial mirror is characterized by a surface that is capable of both reflecting some incident light as well as allowing some light to pass through the mirror. Through the use of a partial mirror (or other partially reflective surface) a viewer may see an object behind the partial mirror at the same time that the viewer sees the image of a second object reflected on the surface of the mirror. The partial mirror-based CT "Image Overlay" system requires independent determination of location for both patient and observer using external 6-degree-of-freedom tracking devices, so as to allow appropriate images to be rendered from pre-acquired CT data.

Another recently developed imaging technology merges ultrasound images and human vision by means of a Head-Mounted Display (HMD) worn by the human operator. The location and orientation of the HMD is continuously determined relative to an ultrasound transducer, using 6-degree-of-freedom tracking devices, and appropriate perspectives of the ultrasound images generated for the HMD using a graphics computer.

These prior art systems may not be appropriate for use with a practical real-time imaging device. Controlling the multiple degrees of freedom can be difficult, and the systems may have too many complex parts to be useful. As such, there is recognized a need in the art to provide a device capable of merging a human's normal vision of an object with an "internal" image of the object that emphasizes freedom of operator movement and/or simplicity of design.

SUMMARY OF THE INVENTION

The present invention contemplates, in at least one preferred embodiment, a device and method for merging human vision of the outside of a target object and a reflected tomographic image of the internal features of the same object. The invention may include an image capture device (e.g., a tomographic scanning device such as an ultrasound transducer), an image display device (e.g., a computer or video monitor), and a half-silvered mirror to "fuse" or superimpose the two images together.

In at least one preferred embodiment, the present invention provides a 2D ultrasound transducer, an image display, and a partially reflective, partially transparent, surface (e.g., half-silvered mirror) generally displaced between a target object and the image display. The transducer, the display, and the mirror may be fixedly attached to each other, or one or more elements may be partially or completely moveable with respect to the others. The movement may be accomplished through direct manipulation by the operator or with the use of one or more robotic arms.

In at least one preferred embodiment, the present invention provides a 3D ultrasound transducer, an image display, and a partially reflective surface broadly displaced between a target object and the image display. The image display may preferably display an appropriate slice of the 3D ultrasound data (effectively a 2D tomographic image) to enable a proper combined image to be seen when an observer looks at the target object through the partially reflective surface.

In at least one preferred embodiment, the present invention includes a series of gears, pulleys, or other motion transfer devices installed between the transducer, the display and the half-silvered mirror to allow the angle between the mirror and display to follow the angle between the transducer and the mirror as the transducer is moved. The present invention also contemplates various embodiments where the transducer is free to move in any direction or where robotic systems allow for the remote performance of procedures.

These and other details, objects, and advantages of the present invention will be more readily apparent from the following description of the presently preferred embodiments.

BRIEF DESCRIPTION OF THE DRAWINGS

For the present invention to be clearly understood and readily practiced, the present invention will be described in conjunction with the following figures, wherein like reference characters designate the same or similar elements, which figures are incorporated into and constitute a part of the specification, wherein:

FIG. 14 shows an embodiment of the present invention utilizing interference principles.

DETAILED DESCRIPTION OF THE INVENTION

It is to be understood that the figures and descriptions of the present invention have been simplified to illustrate elements that are relevant for a clear understanding of the invention, while eliminating, for purposes of clarity, other elements that may be well known. Those of ordinary skill in the art will recognize that other elements are desirable and/or required in order to implement the present invention. However, because such elements are well known in the art, and because they do not facilitate a better understanding of the present invention, a discussion of such elements is not provided herein. The detailed description will be provided hereinbelow with reference to the attached drawings.

The invention contemplates, in at least one presently preferred embodiment, a method and device for merging or superimposing the reflection of a two dimensional tomographic image of the interior of a target object with the normal human vision view of the outside of that same target object. This methodology may be used in any application where viewing the interior of an object is desired, and the methodology is not limited to any particular industry or application. The interior image is preferably captured by any real-time imaging modality, where real-time does not necessarily indicate near-instantaneous display, but only that the target object has not moved significantly since the scanning was performed. One such real-time imaging modality is ultrasound.

Although this methodology and device can be used across many different fields of endeavor, the present invention may find particular applicability in the medical field. Because unwarranted or excessive intrusion into the interior portions of a human body may cause damage, infection, or other unwanted effects, these intrusions should be limited in both the number of instances and the scope of the intrusion. As such, it is preferable to perform subcutaneous procedures with at least some direct sighting of the interior of the patient. Because the medical device applications may be particularly useful, the present invention will be described with reference to such a medical device, but this exemplary disclosure should not limit the scope of this patent to any particular industry or use.

Figure 1:
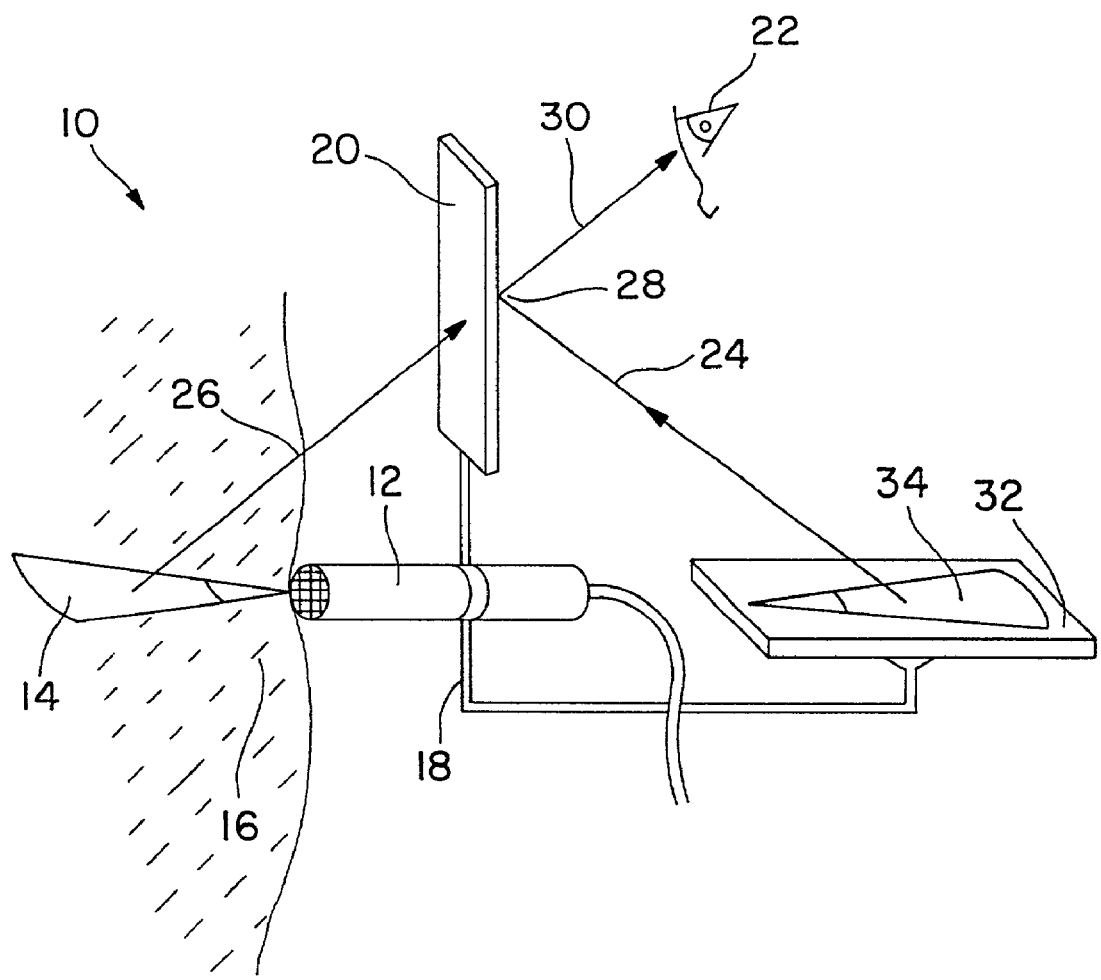
FIG. 1 is a schematic view of a device capable of merging a reflected tomographic image from a 2D ultrasound scanner with a direct view of a target image.

FIG. 1 shows an isometric view of a presently preferred embodiment of an imaging device 10 utilizing a two dimensional (2D) ultrasound transducer 12 capable of taking a B-Mode image slice 14 of a target object 16. In FIG. 1, there is a two dimensional ultrasound transducer 12 fixedly attached to a rigid frame 18. This transducer 12 is preferably a conventional ultrasound transducer that captures a "sonic" tomographic image slice 14 of the interior portion of the target object 16 (in this case a human patient).

Extending vertically from the middle region of the rigid frame 18 is a half-silvered mirror or other semi-transparent, semi-reflective, material 20. The half-silvered mirror 20 allows a user 22 (e.g., a doctor) to look through the mirror 20 at a target object 16 (e.g., a patient) located on the other side of the mirror 20 at the same time that a second image 24 is reflected on the front surface of the mirror (at 28). In this way, the direct target object image 26 and the reflected tomographic image 24 can be combined (image line 30) in the field of view of the user 22.

In FIG. 1, the half-silvered mirror 20 is depicted extending vertically up from the ultrasound transducer 12 midway along the transducer handle, but, in fact, the mirror 20 may be located at some other position in another vertical plane either behind or in front of the depicted vertical plane. More specifically, the FIG. 1 half-silvered mirror 20 could be translated forward or backward (or even tilted) as long as the display 32 is moved in a way that corresponds appropriately (as described in detail below).

At the opposite end of the rigid frame 18 from the transducer 12 is a flat panel display 32 showing the ultrasound image or other tomographic slice 34, with the image portion 34 facing upwards. This display 32 may be any low profile or flat display and may preferably be a liquid crystal display (LCD). When a user 22 looks at a target object 16 through the half-silvered mirror 20, the ultrasound display image 34 will be reflected along line 24 onto the front face of the half-silvered mirror (at 28). The user's sight line 30 will therefore be a combination or superimposition of the direct target object image 26 and the reflection of the ultrasound image 24.

In order to correctly visually merge the reflected ultrasound image 24 with the target object image 26, the ultrasound display image 34 may be reversed (along a horizontal plane), flipped (along a vertical plane), rotated, translated, and/or scaled (depending on the original image 34 location, orientation, and scale on the display 32) so that the reflected ultrasound image 24 on the face of the half-silvered mirror (at 28) correctly portrays the size, scale, and orientation of the ultrasound slice 14 being taken. In a practical sense, if one merely rotates the transducer 12 180 degrees, the ultrasound display image 34 will be flipped exactly as if this image manipulation was accomplished electronically.

A profile of a human operator's eye 22 is shown in FIG. 1 looking through the half-silvered mirror 20 at the target object 16 (patient). Because of well-known laws of light reflection, the ultrasound image 34 on the flat-panel display 32 will be reflected on the operator-side surface of the half-silvered mirror (at 28). Therefore, as the operator 22 looks at the target object 16 through the half-silvered mirror 20, the reflected ultrasound image 24 is merged (superimposed) with or onto the direct target object image 26. To the operator 22, these two images 24, 26 will effectively combine into one image 30 that includes the surface (normal vision 26) of the target object 16 and the interior (reflected ultrasound 24 or other tomographic reflection) of the target object 16. Because the angle of reflection of the ultrasound image follows the operator's sight angle as the operator's head moves, the merger 30 of these two images 24, 26 is independent of the location of the operator 22 (user). Therefore, the user 22 can move his head as well as take full advantage of stereoscopic vision to extrapolate the hidden parts of the invasive tool (e.g., needle) from the exposed parts of the same tool with respect to the anatomical structures in the ultrasound scan.

Because the direct target object image 26 and the reflected ultrasound image 24 are combined or superimposed on the surface of a half-silvered mirror (at 28) that may be naturally within the operator's direct line of sight (along 30), the operator 22 can preferably maintain direct hand-eye coordination throughout the procedure. This natural line-of-sight image combination 30 effectively allows the operator 22 to see "through" the surface (e.g., skin) of the target object 16 and into the underlying structures or layers of materials.

Further, although the present imaging device 10 may be used with virtually any imaging technology, using a nearly instantaneous imaging technology, such as ultrasound allows the interior and exterior views of the target object 16 to be nearly synchronous. However, the method may be applied to any real-time tomographic imaging modality, where "real-time" refers to any imaging modality that can update the displayed image 34 before the patient (target object 16) moves. As patient movement decreases, "slower" modalities become more useful. If a slower imaging technology is used (i.e., there is a substantial lag time between image capture and image display), the operator 22 may instruct the patient 16 to lie still so that the delayed interior image 34 will remain aligned with the current target object image 26. In this way, even a slower imaging technology may be used with the present invention.

Some possible "quick" imaging modalities include ultrasound, cine-CT and rapid MRI. Some "slower" modalities include conventional MRI, conventional CT, SPECT and PET. However, even these slow modalities may create an accurate combined image 30 so long as the target object 16 has not moved since the last image was captured. A needle or other intruding device may still be introduced using the overlaid image for guidance, provided the target object 16 has not moved. To increase the likelihood that the patient remains still, some combination of laser or ultrasonic range-finders, video cameras, and/or motion sensors (not shown) may be used to detect such movement and warn the operator 22 that the image will not be superimposed perfectly (at 28). Alternatively, these same sensor devices could detect exactly how far the target object 16 has moved since the last image capture and electronically correct the displayed image 34 and/or the location of the display 32 or mirror 20 (see below) to compensate for such target object movement.

Figure 2:
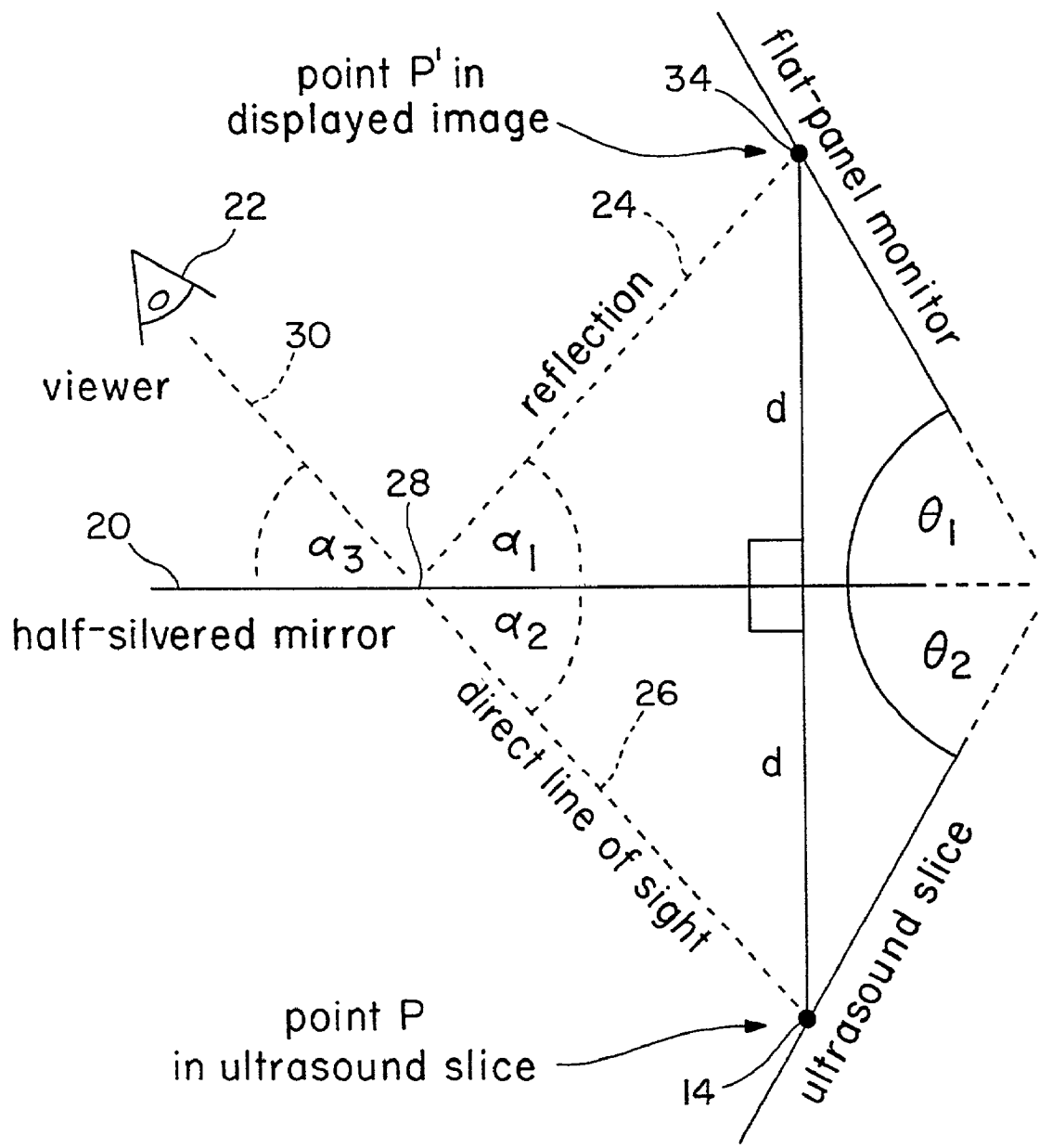
FIG. 2 is a schematic of the image angles that allow the operator to move in relation to the half-silvered mirror while maintaining image merger.
Figure 3:
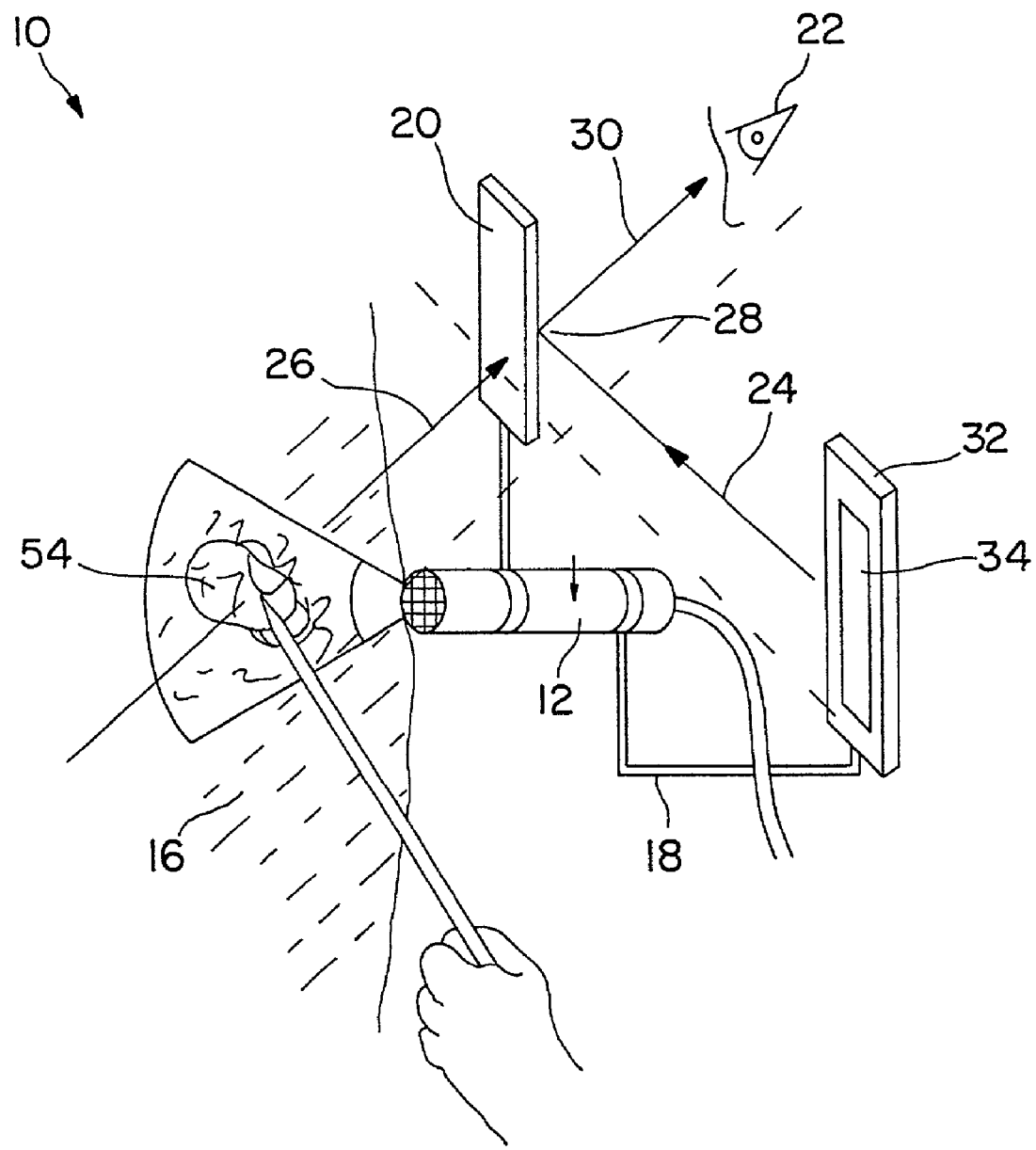
FIG. 3 is a schematic view of a device capable of merging a slice from a 3D scan with a direct view of a target image.

The mathematical requirements for locating the components of the apparatus are shown in FIG. 2. The half-silvered mirror 20 is preferably positioned between the tomographic slice 14 and its image 34 reflected on the flat-panel display, separated from each by the same angle θ ($\theta_1 = \theta_2 = \theta$). In essence, the half-silvered mirror 20 bisects the angle 2θ. As seen in FIG. 3 (below), θ can approach zero. Because the mirror 20 in FIG. 2 bisects the angle 2θ, point P in the ultrasound slice 14 and its corresponding image P' in the flat panel display 34 are both distance d from the half-silvered mirror 20. The line between the point P in the slice 14 and its image P' in the display 34, along which d is measured, is orthogonal to the plane of the semi-transparent mirror 20.

The figure shows the eye of the viewer 22, to whom the ultrasound display will be superimposed (along 30) on the corresponding physical location of the slice irrespective of the viewer's location. The angle of incidence from the flat panel display 34 to the face of the half-silvered mirror (at 28) is labeled $\alpha_1$ in FIG. 2. By well-known laws of light reflection, the angle of reflection $\alpha_3$ is equal to the angle of incidence $\alpha_1$. Because the mirror 20 bisects 2θ and further by well-known laws of geometry, the "incidence" angle $\alpha_3$ from the corresponding point 14 in the target object 16 to the back of the half-silvered mirror 20 is also equal ($\alpha_1 = \alpha_2 = \alpha_3 = \alpha$). In this way, regardless of viewer position, the direct target object image 26 and the reflected tomographic slice image 24 will always coincide to combine image 30.

FIG. 3 shows a presently preferred embodiment of the imaging device 10 utilizing a three dimensional (3D) ultrasound transducer 12. As with the 2D transducer described above, the FIG. 3 embodiment details a half-silvered or partial mirror 20 fixedly attached to the transducer 12 and extending vertically upwards therefrom. In this embodiment, the transducer 12 is capable of capturing 3D imaging data of a scanned volume 54 (e.g., a Real Time 3D (RT3D) ultrasound image). The image 34 that is shown on the flat-panel display 32 (and therefore reflected 24 onto the partial mirror 20) is preferably a 2D tomographic slice through the scanned volume 54 in the target object 16 (for example, a "C-Mode" slice, parallel to the face of the transducer 12). This 2D tomographic image 34 may be mathematically computed from the collected 3D imaging data by a computer (not shown). The flat-panel display 32 should be properly located and oriented to precisely reflect 24 onto the half-silvered mirror (at 28) the location of the corresponding tomographic image within the target object 16. Once again, the image 34 on the display 32 is preferably electronically translated, rotated, scaled and/or flipped to complete proper registration independent of viewer location, as necessary.

Compared to the "Image Overlay" CT-based system using previously obtained data or any other "lagging" imaging scheme, ultrasound or other "real-time" data is preferred so that the present location of the patient (target object) 16 need not be independently established or registered by the imaging device. Whatever is currently in front of the transducer will simply appear superimposed on the operator's visual field at the appropriate location. Furthermore, the present invention preferably displays only a single slice, as opposed to a complete 3D rendering as in the "image overlay" CT system (described above). Therefore, the visual image merger 30 can be made independent of the observer's location simply by placing the ultrasound display 32 where its reflection 24 in the half-silvered mirror 20 superimposes on the direct view 26 of the target object 16. Since the displayed tomographic image 34 is 2D and is reflected precisely on its proper location in the target object 16, the correct combination 30 of these views 24, 26 is independent of viewer 22 location. This may be simpler and more efficient than superimposing 3D renderings.

The devices and methods as described above include rigidly attaching a semi-transparent mirror 20 and flat-panel display 32 to the tomographic scanning device 12 (or other image capture device). This rigid fixation and the associated bulk of the complete device 10 may reduce the ability of the operator 22 to manipulate the scanning device or transducer 12 during a procedure. There are several ways in which the freedom and ability of an operator 22 to manipulate the image capture device 12 may be increased.

For example, a linkage system of levers, weights, pulleys, and/or springs (not shown) could be constructed, while maintaining the rigid relationship between the device components (scanner 12, mirror 20, display 32), to aid in the manipulation of the entire apparatus 10. This linkage system of levers, weights, pulleys, and/or springs may cantilever or otherwise reduce the amount of force necessary to manipulate the apparatus 10. A similar configuration, for example, is often used in hospitals to aid in the manipulation of heavy lights during surgery. These levers, weights, pulleys, and/or springs are preferably attached to the ceiling or to a floor stand.

Alternatively, the operator 22 may obtain greater flexibility to manipulate the transducer 12 through a system of gears and/or actuators that keep the angle ($\theta_1$) between the display 32 and the half-silvered mirror 20 equal to the angle ($\theta_2$) between the transducer 12 and the mirror 20. As the user 22 moves the transducer 12 in various ways, additional gears, actuators, and/or encoders of linear and/or angular motion could accommodate this transducer motion (and corresponding change in $\theta_2$) by providing equivalent motion of the displayed ultrasound image 34 (and corresponding change in $\theta_1$) through physical manipulation of the display screen 32 and/or electronic manipulation of the image 34 displayed on the screen 32. These gears, actuators, and/or image manipulations preferably keep the appropriate angle ($\theta$) and location between the display 32 and the half-silvered mirror 20 so that the user 22 can move the transducer 12 and still see a proper combination image 30 of the target object image 26 and the reflected ultrasound image 24 independent of viewer location. Such a system could be made to accommodate 6 degrees of freedom for the transducer, including 3 rotations and 3 translations. As with the above embodiments, this embodiment preferably entails physical attachment of the transducer 12 to the rest of the apparatus (which may hinder use of the device 10).

Figure 4:
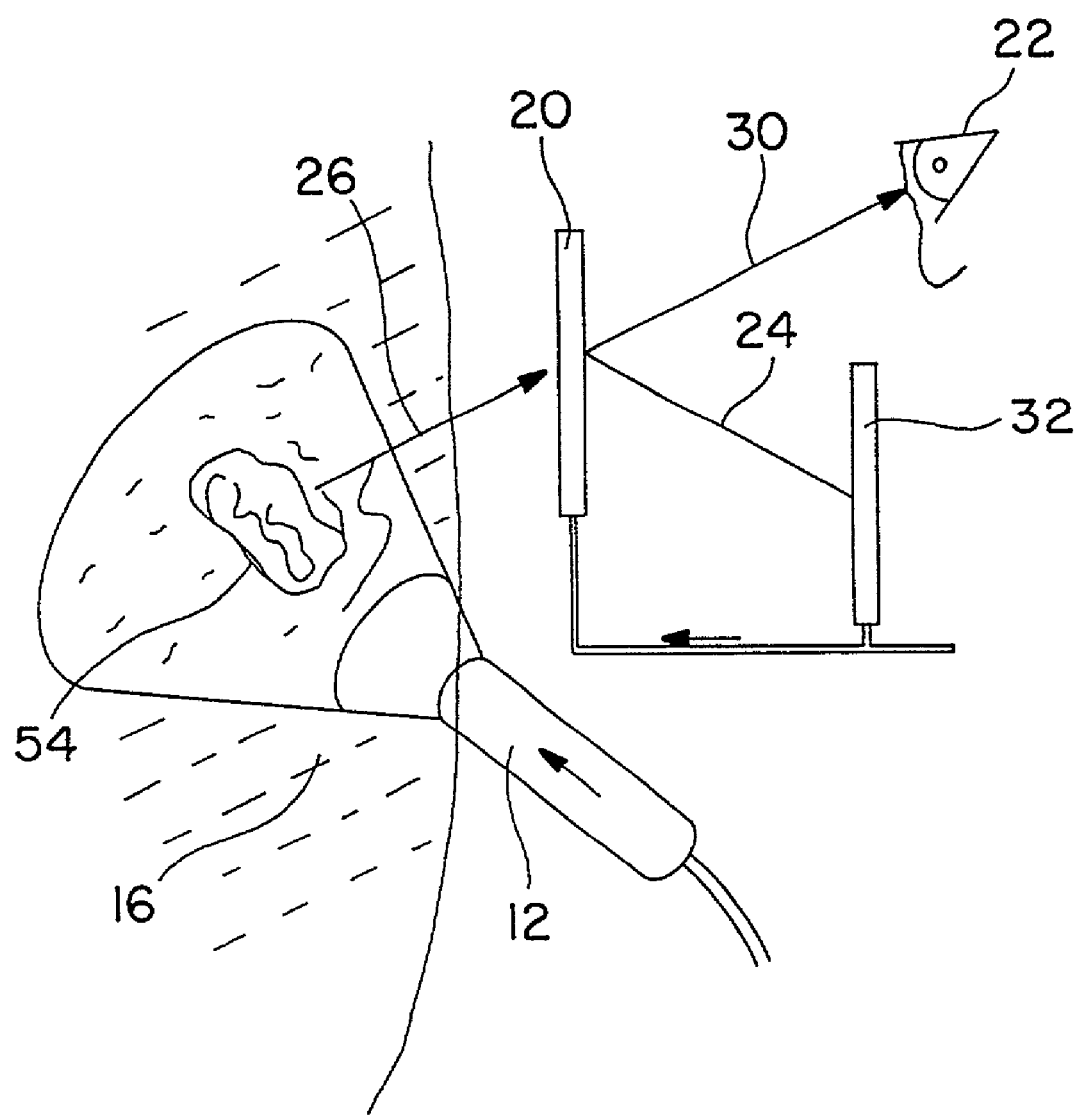
FIG. 4 is a schematic view of an imaging system with the image capture device removed from the remainder of the system.

To further increase the ability of the operator 22 to manipulate the transducer 12 (or other tomographic scanning device), the transducer 12 (or other image acquisition device) may be physically freed from the rest of the apparatus. By continuously determining the relative angles and location of the transducer 12 with respect to the half-silvered mirror 20 using a system such as the commercially available "FLOCK-OF-BIRDS" or "OPTITRACKER" systems, the angle ($\theta_1$) and orientation of the display 32 with respect to the mirror 20 could likewise be adjusted to compensate for this transducer manipulation. One embodiment of a system for freeing a 3D ultrasound transducer 12 is shown in FIG. 4. The appropriate slice through the 3D ultrasound data 54 is computed and displayed (on display 32) so as to effect a merger 30 of the two images 24, 26 on the face of the mirror 20.

Similarly, for 2D ultrasound, the manipulability of the transducer 12 may be especially important when searching for a target. The problem can preferably be addressed by detaching the transducer 12 from the rest of the assembly (the mirror 20 and the flat-panel display 32). A 6-degree of freedom tracking device such as the "FLOCK-OF-BIRDS" or "OPTITRACKING" system may be attached to the handle of the transducer 12. The flat-panel display 32 may be detached from the mirror 20 and controlled by a series of motors such that the display 32 would be made to remain exactly in the reflected plane of the ultrasound slice, as determined by the tracking system on the transducer handle. Such display movement will preferably occur according to well-known principles of robotics.

Such a motorized device may lag behind the movement of the transducer 12 during rapid manipulations of the transducer 12 by the operator 22, but would preferably catch up with the operator at relatively motionless periods when the operator 22 had located a desired target. The mirror 20 may preferably be held motionless relative to the target object 16, establishing the frame of reference for both the transducer tracking system and the motorized display 32. Alternatively, the mirror 20 may be motorized and the display 32 held constant (or both the mirror and the display could move).

The other degrees of freedom which may be necessary to visually fuse 30 (superimpose) the displayed ultrasound image 24 with the actual target image 26 may be supplied by graphical manipulation of the displayed image 34 on the flat-panel display 32, based on the tracking of the transducer 12. As with the fixed and geared assemblies described above, the motorized display 32 and graphical manipulation of the displayed image 34 preferably provides visual "fusion" 30 of the reflected ultrasound image 24 with the actual target object image 26 independent of operator 22 or target object 16 location.

In one presently preferred embodiment of the invention, two robotic arms, or a single paired robotic device, manipulate both the transducer 12 and the display 32 (and/or the mirror 20) under remote control in such a way that the visual fusion 30 is maintained. This may eliminate the need to track the transducer 12, replacing it with feed-forward remote control of the transducer location via a joystick or other controller. The simultaneous control of two robotic devices whose motions may be as simply related as being mirror images of each other, may be accomplished in a fairly straightforward manner, and may exhibit a more synchronous image fusion.

A natural pivot-point for the display monitor may be the reflection of the point of contact between the transducer and the target object because, during many procedures, the operator tends to rotate the ultrasound transducer in all three rotational degrees of freedom around this point (to find a desired target). Thus, for the simultaneous control of two robotic devices just described, rotating the display monitor with three degrees of freedom around this point may be preferred. For systems that move the display while tracking a manually manipulated transducer, at least one translational degree of freedom may be needed to allow the display monitor to become coplanar with the ultrasound slice.

Calibration of the fixed system and development of the servo-linked (motorized) display system or the dual robotic system just described may require careful consideration of the degrees of freedom in the registration process. First, consider only the geometric transformation, i.e., assume the scale of the captured slice and the displayed image are identical and undistorted. To complete the geometric transform registering the reflection of the ultrasound image to the actual slice, we need to satisfy 6 degrees of freedom. First we have 3 degrees of freedom to manipulate the display physically into the plane of the slice reflection. This can take the form of two rotations to make the display screen reflection parallel to the slice and one translation orthogonal to the display screen to bring it into precisely the same plane.

Once the display reflection and the slice are in the same plane, we need 3 more degrees of freedom to match the image and the slice, which may be achieved through two translations and one rotation of the image on the display. In essence, the 6 degrees of freedom place the display in the proper physical plane to reflect the image on the half-silvered mirror (3 degrees of freedom) and then rotate and translate the image on the display so that the correctly placed reflection is properly aligned (3 additional degrees of freedom) on the mirror with the actual target object image.

Beyond the geometric transformation, further calibration may be required. First, the proper scale must be calibrated. This includes isotropic scale (similarity transform) and non-isotropic scale (affine transform). Further corrections may be required for non-linear geometry in both the imaging system and the display by warping of the image.

To the extent that the geometric properties of the slice do not change with tissue type, and the slice geometry does not change as the transducer is moved relative to the target object, calibration of the system 10 may only need to be performed initially, using a phantom target object (not an actual patient). Such calibration will suffice for slice geometry due only to the scanner. Further changes in image geometry due to tissue properties will depend on transducer location relative to the tissue. These changes may be due to differences in the speed of sound in different tissue types. It may be possible to correct for these using image analysis techniques as known and developed in the art.

A problem with calibration may arise because a phantom in a water tank that is easily scanned using ultrasound will appear displaced to human vision due to refraction at the air-water interface. Several solutions are described here to this problem. One solution may use a rod that intersects both the reflected image (in air) and an ultrasound slice displaced along the rod (water). The display may then be physically moved or rotated, and the image on the display may be electronically moved or rotated, to make the rod appear to intersect the corresponding reflected ultrasound image appropriately.

A second calibration solution includes the use of a calibration phantom. The phantom is placed in water or some other ultrasound transmitting (but light refracting) medium and scanned by the image capture device. The image is "frozen" (still picture) on the display and reflected off of the half-silvered mirror. Without moving the calibration phantom, the water or other medium is drained or removed from the calibration setup. The user can then adjust the display or the image on the display until the "frozen" reflected scan image of the phantom aligns with the direct sight image of the calibration phantom. Many other calibration schemes could be used within the scope of the present invention.

Figure 5:
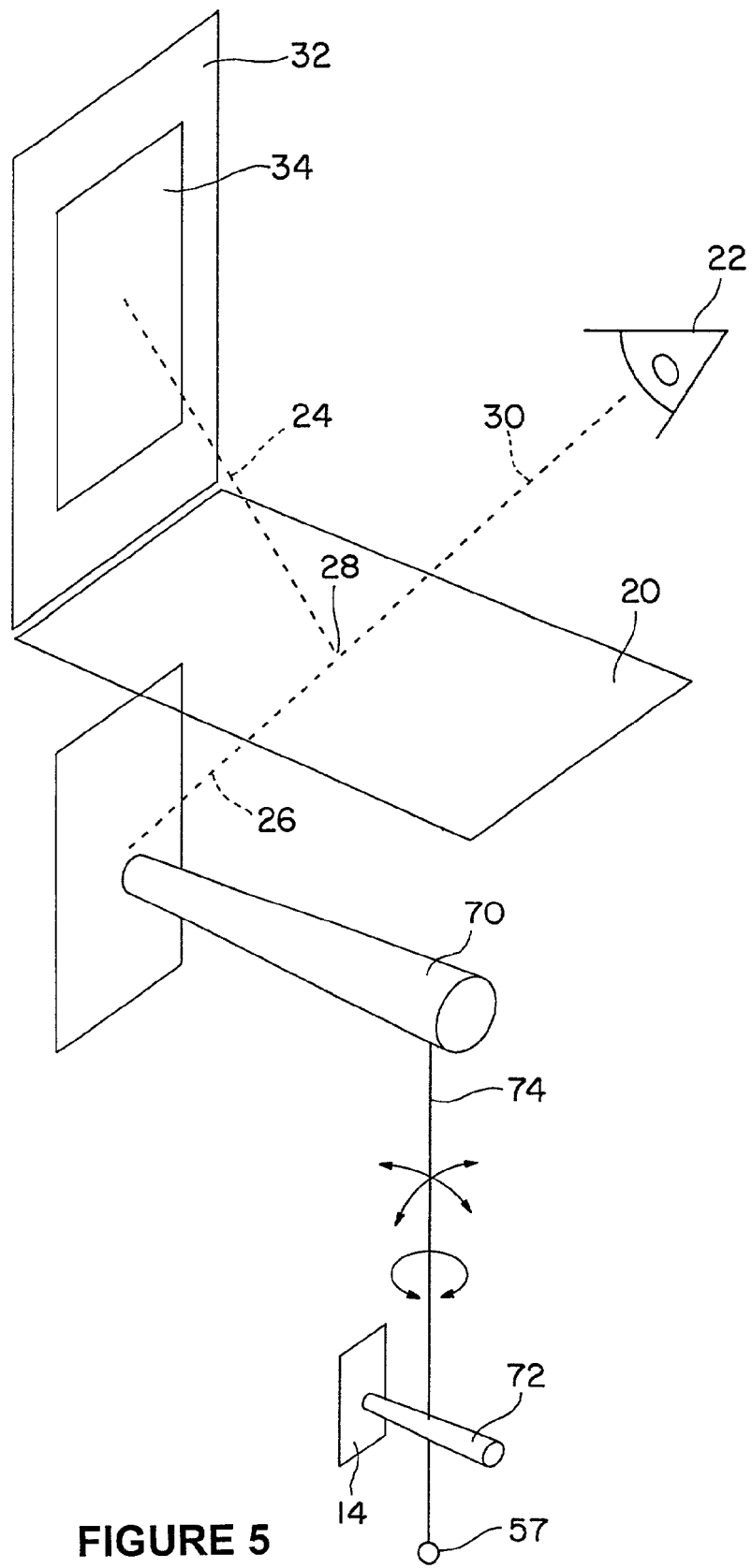
FIG. 5 shows the methodology applied to remote operation using a mock effector in the field of view.
Figure 6:
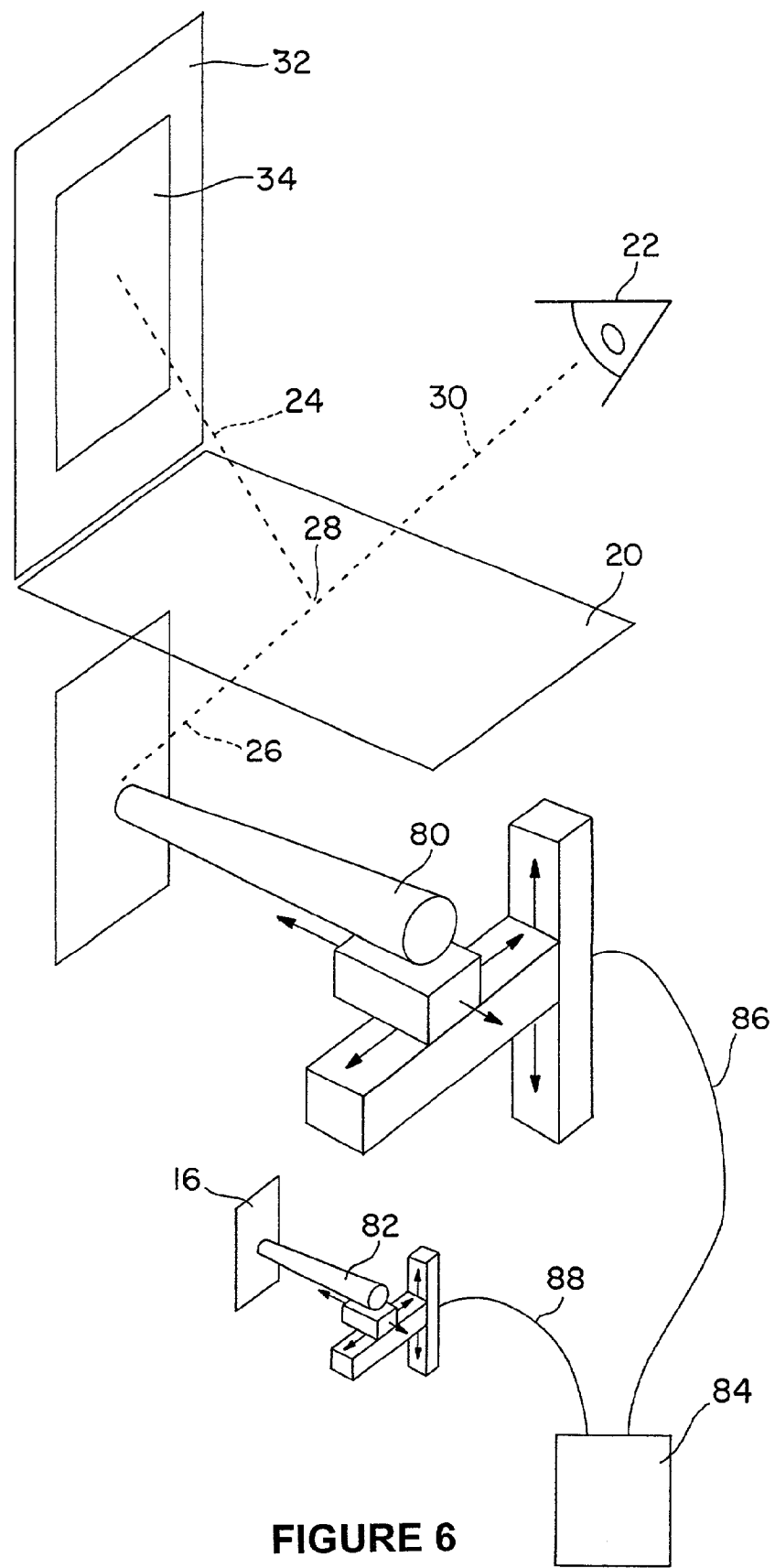
FIG. 6 shows the methodology applied to remote operation utilizing a remote-controlled effector.

In one presently preferred embodiment of the present invention, a "remote" procedure is performed through the use of a tomographic scanning device and surgical implements controlled remotely with a mechanical or robotic "mock effector" in the operator's field of view instead of the actual target object being in the operator's field of view. A mock effector is a physical replica of the actual invasive instrument, preferably of identical shape but not necessarily identical scale. The mock effector may either be directly controlled by the operator (FIG. 5) with mechanical linkages, encoders and/or tracking devices relaying the desired motion to the actual effector, or alternatively the operator may use a remote control to activate both the mock effector and actual (surgical) effector with corresponding motions (FIG. 6).

For example, a procedure may involve using a hypodermic needle or micro-pippette to take samples in a certain plane. In FIG. 5, the tomographic scanning device (not shown) may be aligned to capture a slice 14 of the target object from which the sample may be taken. The action of the actual surgical needle 70 may be controlled remotely by operator 22 manipulation of a mock effector (needle) 70 in the user's field of view demonstrating the precise motion of the actual remote effector 72, although possibly at a different scale. The scale (as well as the location and orientation) of the mock effector 70 would match that of the reflected tomographic image 24 (to make the combined image 30 an accurate representation).

In this example, a mock needle 70 may be present in front of the operator 22 (remote from the target object). The operator 22 preferably looks through the half-silvered mirror 20 at the end of the mock effector 70. The operator's field of vision is a merged image 30 of the direct view 26 of the mock effector and the reflection of the tomographic slice 24. If the actual needle 72 performing the procedure on the patient (target object 16, not shown, through which tomographic slice 14 is acquired) is of a different scale than the mock effector needle 70, then the tomographic image 34 displayed on the monitor 32 is preferably moved and/or scaled so that the reflected tomographic image 24 and the direct view 26 of the mock effector are of equal size, scaling, and orientation at the surface 28 of the half-silvered mirror 20.

The mock effector needle 70 and the actual surgical effector needle 72 are preferably connected through some sort of control mechanism 74. In FIG. 5, this control mechanism is shown as a direct mechanical link 74, being a rod fixed at one end by a ball-and-socket 57 to allow 3 degrees of rotation. As the operator manipulates the mock effector 70, the actual effector 72 will move correspondingly (although on a smaller scale). Similarly, the control mechanism may be some type of tracking or encoder device that registers the movement of the mock effector 70 and transfers this movement to the actual surgical effector 72. In this way, the operator can manipulate a mock effector 70 and cause a procedure to be performed on a target object at a remote location.

This remote procedure model may be useful for extremely small scale procedures. For example, assume a microscopic region of a patient must be cut (e.g., a cancer cell removed or a cornea operated upon). In the region of a very small cutting implement, a specialized tomographic scanning modality (such as Optical Coherence Tomography (OCT) or a high frequency (100 MHz) ultrasound) may be used to capture an image slice. At a remote location, a doctor may preferably look through a partial mirror with a reflection of the tomographic slice on its face superimposed upon a mock cutting implement whose motion is linked to that of the actual cutting implement. Although the actual procedure occurs on a microscopic scale, both the tomographic slice and the mock effector can be magnified or scaled up to a point that allows the doctor to perform the procedure in a more relaxed and accurate manner. As long as the mock effector is scaled up to a similar size as the tomographic slice, the overlay of the images may be accurately located and oriented with respect to each other. In this way, small scale medical (or non-medical) procedures may be easier to perform. Similarly, large scale procedures such as undersea robotics using sonar-based tomographic imaging may be performed remotely at a smaller scale than they actually occur.

FIG. 6 details one possible robotic version of the present invention. The FIG. 6 remote application is generally similar to the FIG. 5 implementation with the addition of a control box 84 used to control the motion of both the mock effector 80 and the actual surgical effector 82. As in the previous example, the operator 22 looks through the surface of the half-silvered mirror 20 at the working end of a mock effector 80. A tomographic image 34 of the target object 16 is displayed on a monitor 32 and reflected along line 24 onto the surface of the half-silvered mirror 28. The operator's filed of view includes the merger 30 of these two images 24, 26.

In this example, however, the operator 22 preferably does not directly manipulate the mock effector 80. Instead, some type of control, for example a joystick, keyboard, voice activated software, or other device, is manipulated by the operator 22. This control device causes the movement of both the mock effector 80 (through control line 86) and actual effector 82 (through control line 88). In FIG. 6, each of these effectors 80, 82 can be moved with 3 degree of freedom movement. The mock effector 80 can again be scaled larger or smaller to make the manipulation of the actual effector 82 more convenient. Preferably the size, scale, and orientation of the tomographic image 34 displayed on the monitor 34 is matched to the size, shape, and orientation of the mock effector 80.

For robotic versions of the present invention, the effector 82 that interacts with the patient 16 need not necessarily be a mechanical surgical tool. For example, the effector could be a laser, RF (radio frequency) transmitter, or other device for delivering or imparting energy or matter on a target object. In these cases, the mock effector used by the operator may include some kind of demonstration of the energy or matter delivered, either expected or measured, to the patient. For example, an isosurface of expected RF field strength may be physically constructed and mounted on the mock effector used by the operator such that the field model intersects the reflected image appropriately. In this way, the operator can take into account the field of the effector's use, as well as the effector itself.

The present invention may also depend on the lighting used on or around the device. For example, light that hits the surface of the half-silvered or partial mirror from above (operator-side) may introduce unwanted reflections in the semi-transparent mirror. In this case, the target object will be more difficult to see. Alternatively, light that comes from a source beneath the half-silvered mirror (on the same side of the mirror as the target object) may increase the clarity of the target object image without introducing unwanted light reflections onto the half-silvered mirror. Various types of lighting (visible, ultraviolet) as well as paints, markings, and light emitting markers on the targets or tools themselves may have different properties that are adjustable to change the contrast, intensity, and interpretability of the image superimposition.

Alternative forms of light may also be used to register locations in the ultrasound during a procedure. These alternative light sources can be used to identify certain features of the target object in addition to the 3D visual cues inherent to superimposition of the reflected image. For example, a plane of laser light can be created with a movable mirror and a laser such that any real object (part of target object or mock effector) that intersects the plane of laser light will be "marked" by the colored lines of the laser light. Such a laser marking system could be used with a computer vision system to permit automated detection and location determination of the intersection point of the located object and the light plane. This system may be used for automated calibration with corresponding features detected in the tomographic image.

Light sources could also be arranged relative to opaque shields so that only certain parts of the target object are illuminated, such as all parts beyond (or nearer to) the reflected tomographic image. Thus the image would fall on what would effectively be a clipping plane through the object, with all parts of the image closer to (or further from) the viewer not illuminated. Sound, tactile, and/or other forms of feedback may be provided to the operator based on the location of tools relative to the reflected image. These feedback indicators may alert the operator when contact is made, for example between the tip of a needle and the reflected slice.

Various techniques may be used to alter the image as viewed on the low-profile display. The image may be rotated, translated, scaled, or distorted, as previously described, or otherwise cropped or manipulated in many ways according to the needs of the user of the system. For example: extraneous parts of the image may be removed; specific anatomical targets may be automatically identified and graphically enhanced; surgical tools may be tracked and their hidden sections graphically simulated; and/or other useful information may be superimposed on the displayed image for the operator relating to the invasive procedure.

In all, the present invention may be useful for many medical procedures including amniocentesis; many forms of surgery; soft tissue biopsy of organs such as liver, kidney, or breast; and procedures such as the insertion of central venous lines, or even peripheral intravenous catheters. In brain surgery, for example, deformation of the brain after removal of portions of the skull leads to inaccuracy of registration in non real-time modalities such as conventional CT. Real-time guidance using ultrasound may compensate for such deformations, as well as provide adaptive guidance during the removal of an abscess, for example, or in other cases where structures may change shape or location during procedures. Another example is monitoring and correction of tissue infiltration during the infusion of cancer drugs into large veins. The invention may positively effect the success and flexibility of these and other invasive procedures.

Since the visual image merger is independent of viewer location, two or more human operators may work together in the same field of view, assisting each other manually and/or offering consultation. The invention may be valuable in teaching, for example, by clarifying the content of ultrasound images through its location in the target object.

As briefly mentioned above, the version of the device using a mock effector could be used at microscopic scales, for example, to insert micro-pippettes into individual cells under OCT guidance to gather intracellular samples to determine whether the cells are of a cancerous nature (or to deliver therapy to a single cell). Other possible examples include the use of very high frequency ultrasound to guide microscopic surgery on the cornea, and high resolution MRI to guide biopsies of tissue samples of small animals. It may also be used to guide the administration of radiation and other non-invasive procedures, to guide procedures at the end of a catheter or endoscope equipped with a tomographic scanner, or in many other technical and non-technical applications.

One or more of the above embodiments may be oriented toward a portable version of the present invention. The size, shape, and materials used may be minimized so that the entire apparatus can be carried by a single user (or a few users) to the site of a procedure. An ultrasound transducer is preferably used in the portable embodiment because of its small size and ease of use. These embodiments may be especially suited for use in the battlefield for the removal of foreign bodies such as bullets or shrapnel.

Figure 7:
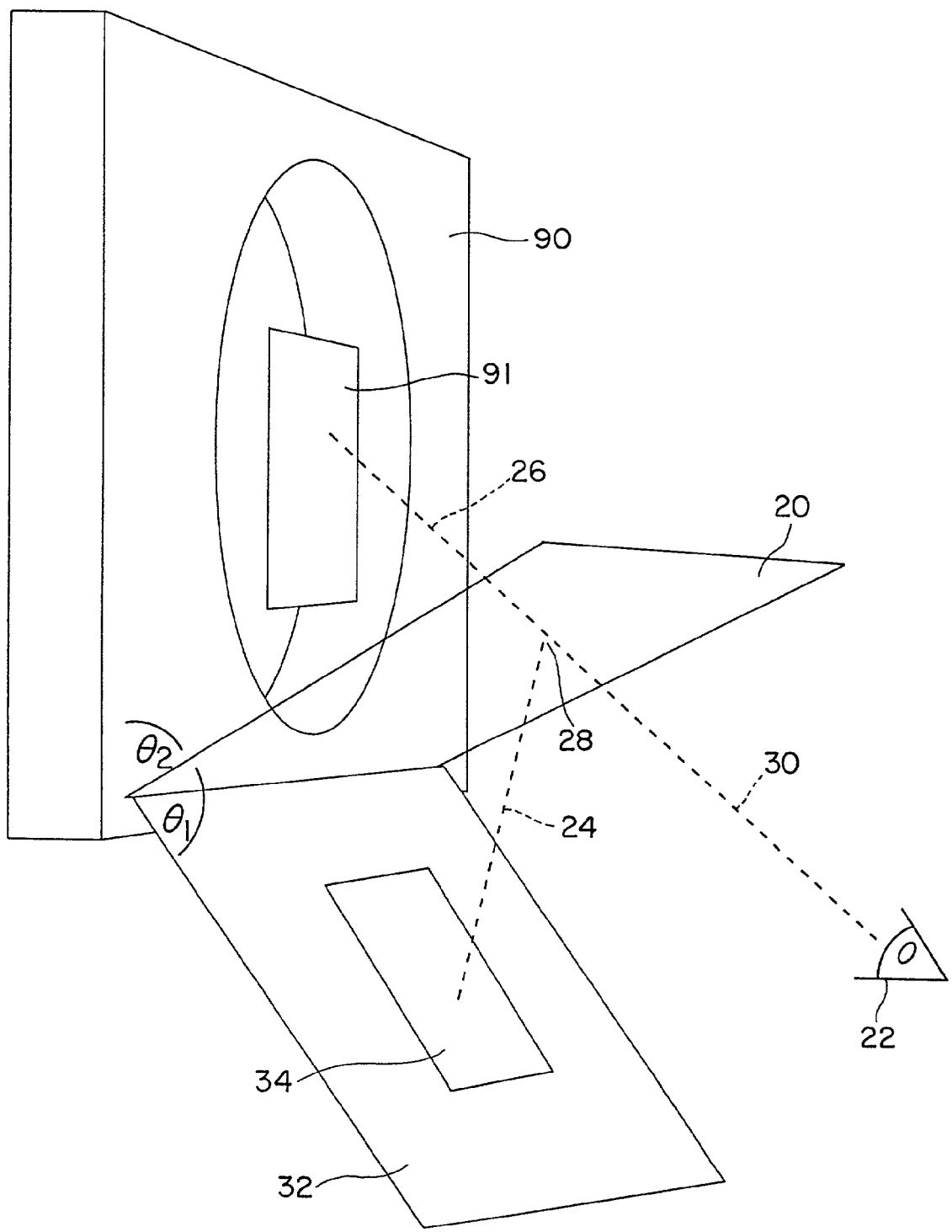
FIG. 7 is a schematic diagram of the present methodology applied to the front of a large imaging machine such as a CT scanner.

The ultrasound transducer in the above portable version may be replaced (towards the opposite end of the size spectrum) with a comparatively massive CT or MRI scanner (see, FIG. 7). The principle of operation is still based on a controlled geometric relationship between the scanner, the mirror 20, and the display 32, just as in the above embodiments. In essence, the angle ($\theta_1$) between the display 32 and the half-silvered mirror 20 should be equal to the angle ($\theta_2$) between the mirror 20 and the slice 91 through the target object within the gantry of the CT or MRI scanner 90.

The image from a CT or MRI machine can often be converted into an appropriate tomographic slice within less than one minute from the image scanning. Once a CT scanner is no longer transmitting X-rays (after the image is captured), there will be no harmful exposure to the operator. As seen in FIG. 7, the gantry 90 of these machines may provide ample access for a doctor or other user 22 to perform an invasive procedure on a patient within the CT machine. Furthermore, if the space in the gantry 90 is not sufficient for a particular procedure, the patient (or other target object) may be moved out of the machine a known distance, and the image 34 of the tomographic scan may then be shifted by that same amount (provided the patient did not move in any other way).

There are many other embodiments and alternatives that may be used in combination with the general structures of the present invention as described above. For example, a jig can be used to "store" the geometric relationships between the image acquisition device (tomographic scanner) and the target object to allow for the use of the invention without the image acquisition device being present upon viewing.

Figure 8A:
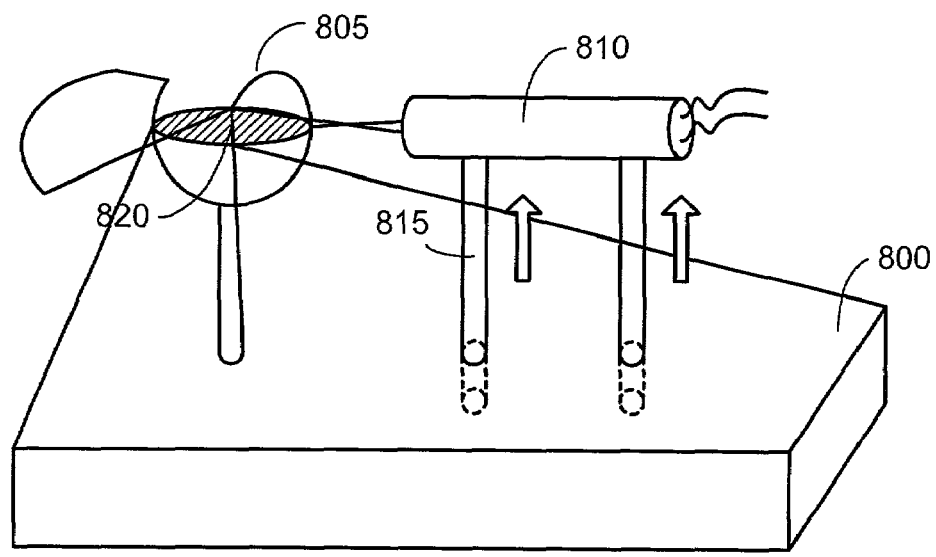
FIG. 8 shows an image acquisition device inserted into a jig (8A) and the jig with the image acquisition device replaced with a screen/mirror apparatus (8B)

FIG. 8A shows one exemplary embodiment of a jig 800 that may be used to store the geometric relationships of the system. The target object 805 and the image acquisition device 810 (in this case an ultrasound transducer) are mounted in a jig 800 using one or more pegs 815. The jig 800 is used to define the spatial relationships between the ultrasound transducer 810 and the target object 805. Once in position, a tomographic slice image 820 of the target object 805 can be obtained and stored for later use.

Figure 8B:
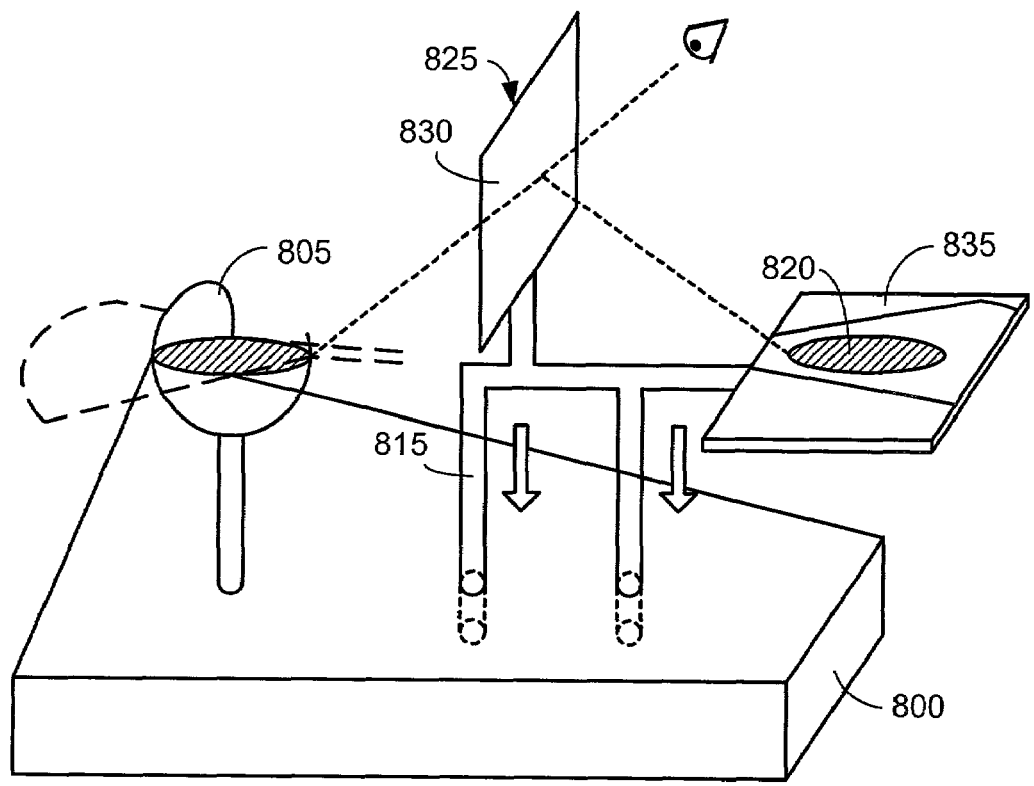

FIG. 8B shows the same jig orientation with the data acquisition device removed. In its place, a display assembly 825 is inserted into the jig 800. In much the same way as previously described embodiments, FIG. 8B shows a half-silvered mirror (partially reflective surface) 830 oriented between the viewer's eye and the target object 805. Further, a flat panel or other display 835 is connected to the jig 800 such that it reflects a captured image onto the user-side face of the half-mirrored surface 830.

If the image capture device 810 from FIG. 8A is used to capture an image 820 of the target object 805, and the flat panel display 835 of FIG. 8B is used to display the captured image 820 at a later time, the reflected view of the interior portion of the target object 805 will be superimposed on the direct view of the target object 805 on the surface of the half-silvered mirror 830. Because the jig 800 keeps the geometric orientations between the target object 805, mirror 830, image acquisition device 810, and display 835 such that the desired relationships described above are satisfied, the jig 800 can be used to make real-time use of the image acquisition device 810 unnecessary for certain applications. The captured tomographic image 820 will not be in real-time, but may still be useful if the target object is kept motionless (or nearly motionless) during a procedure.

As described above, the present invention needs to be calibrated before use to ensure proper orientation of the components and display of the captured image. Specifically, the flat panel display must be oriented with respect to the half-silvered mirror such that the reflected tomographic image is correctly superimposed on the direct view of the target object through the half-silvered mirror. This includes calibrating with both a geometric transform to ensure that the slice and display are coplanar and an affine (or other) transform to scale the ultrasound slice to its correct size, to adjust its aspect ratio, and to correct for skewing. Improved methods for both types of calibration are now given.

Certain computers (e.g., SILICON GRAPHICS O2) are capable of mapping a video image through an affine transform (or other transforms) in real-time. The affine transform permits the tomographic slice displayed on the monitor to be translated, rotated, and anisotropically scaled. The calibration process becomes a matter of finding the optimal parameters for the affine transform.

Mapping location (x,y) to (x',y') with an affine transform is accomplished by multiplying the homogeneous form of (x,y) by a 3×3 matrix A. As shown in equation (1), an affine transform is capable of mapping any triangle to any other triangle. If the mapping for 3 locations is known, the computer can solve for the matrix A. Since matrix A has only six unknown elements, it will have an explicit solution (assuming the 3 locations are not collinear).

$$\begin{vmatrix} x'_1 & x'_2 & x'_3 \\ y'_1 & y'_2 & y'_3 \\ 1 & 1 & 1 \end{vmatrix} = \begin{vmatrix} a_{1,1} & a_{1,2} & a_{1,3} \\ a_{2,1} & a_{2,2} & a_{2,3} \\ 0 & 0 & 1 \end{vmatrix} \begin{vmatrix} x_1 & x_2 & x_3 \\ y_1 & y_2 & y_3 \\ 1 & 1 & 1 \end{vmatrix} \quad (1)$$

Based on this theory, a "bead phantom" may be constructed with three (or more) training beads suspended in roughly an equilateral triangle generally in the plane of the tomographic slice being taken. An uncalibrated tomographic slice image from this phantom (which may be suspended in a water tank) will be captured and displayed on the flat panel display. The water (or other fluid) will then be drained to avoid diffraction errors at the air-water interface during visual inspection. The affine transform may then be found that maps the locations of each of the three training beads in the stored ultrasound image to its corresponding visual location (as seen through the half-silvered mirror). Assuming that the beads in the phantom are actually in the plane of the slice, the calibration process will be independent of viewer location.

Figure 9A:
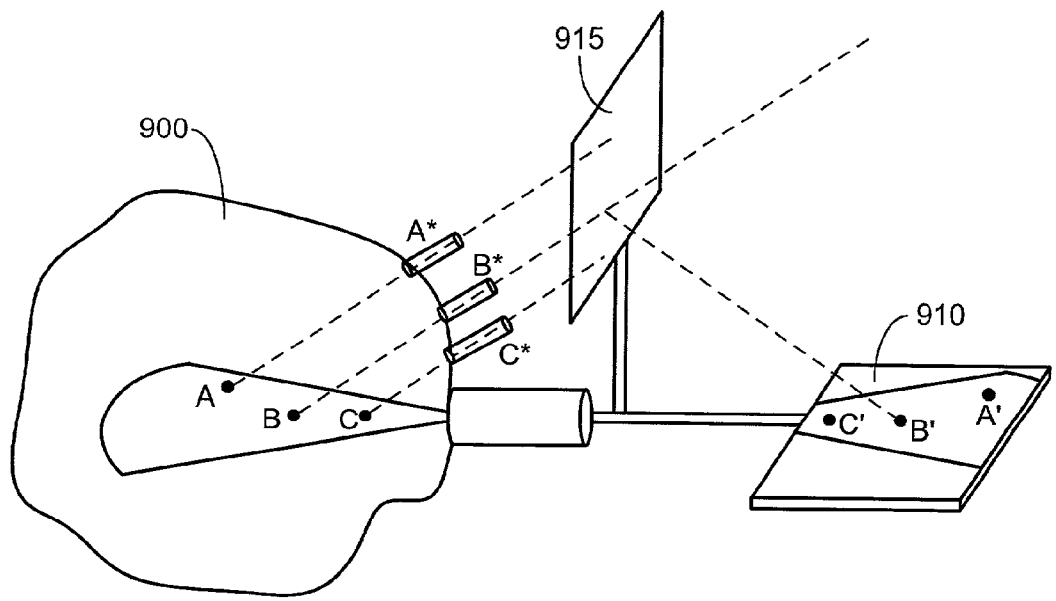
FIG. 9 shows a calibration system for the present invention (9A) with exploded views of tubes attached to the target before (9B) and after (9C) gel is added.
Figure 9B:
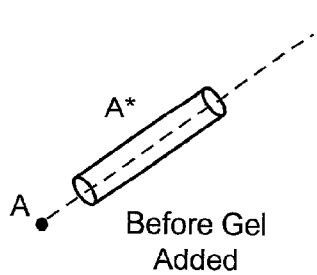

FIG. 9 shows one exemplary embodiment of an improved calibration method for the present invention which may be used to verify the above calibration method. FIG. 9A shows a calibration target object known as a phantom 900. The phantom 900 contains three (or more) targets (A,B,C) inside its surface. In FIG. 9A, the phantom 900 is shown with three beads A,B,C suspended by a thread which is not shown for clarity. The phantom 900 is subsequently filled with a gel or other fluid (to enable tomographic imaging). Three tubes A*,B*,C* are mounted on the exterior surface of the phantom 900 such that each is pointed at its corresponding interior bead (i.e., when looking through the tubes A*,B*,C*, the corresponding target bead A,B,C will be seen). The tubes may be placed after the target beads are in place, or the beads (or other targets) may be inserted using thin rods through the tubes as a guide for insertion (see, FIG. 9B).

Figure 9C:
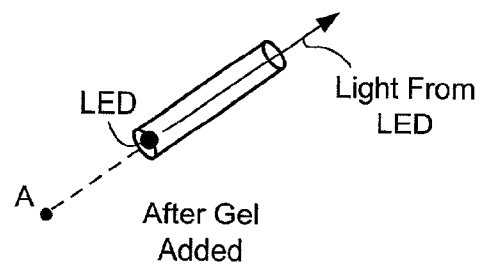

In either case, after the tubes A*,B*,C* and target beads A,B,C are fixed into position, a small LED, light source, or other visual indicator is preferably inserted into the base (phantom side) of each tube A*,B*,C* (see, FIG. 9C). These LEDs can be seen by the viewer looking through the half-silvered mirror when the viewer is looking parallel to the long axis of the tube. After the gel is inserted in the phantom and the LEDs are in place, the viewer can determine that he or she is looking directly at a target bead A,B,C by seeing the corresponding LED through its tube A*,B*,C*.

The slice through the three target beads A,B,C displayed on the flat panel display 910 as A',B',C' is reflected on the face of the half-silvered mirror 915. The corresponding reflections of the displayed images of each target bead A',B',C' can be aligned with the appropriate LED (in direct view) by using three independent (x,y) translations to calculate an affine transform as described above. The co-planarity of the display's reflection and the ultrasound slice will have to be pre-established (through conventional techniques or as described below), and the three target beads will have to be visible in the ultrasound slice. Given all of the above, a virtual target can then be displayed, a needle (or other tool) may be inserted, and the geometric error can then be determined by measuring the intersection of the needle in the ultrasound slice relative to the displayed virtual target (anywhere in the image assuming linearity).

In addition to the affine transform described above, the components of the system must also be geometrically calibrated. Specifically the tomographic slice being captured must be coplanar with the flat panel display being reflected onto the half-silvered mirror in order for the simple geometric relationships of the present invention to be satisfied. The present method replaces an ad hoc "by eye" approach with a method in which targets within the slice and the virtual image are optically determined to be coplanar using a video camera. The method may be undertaken either by the plane of focus of the video camera or by the camera's exhibition of zero parallax when it is moved to a different location.

For the focal plane approach, the water (if any) would be drained from a tank holding the target to permit direct viewing of the target (such as beads on a string). Initially, the target beads and virtual image are viewed through a video camera. The plane of focus of the camera would then be changed in some measurable way. If the target bead were coplanar with the virtual image on the display, the video images of both would go in and out of focus simultaneously. Analysis of the frequency of the spectra of the video image sequence would reveal a single frame with a maximum high frequency. Two such frames, however, would be observed if co-planarity had not been achieved. After adjustments, this geometric calibration confirmation could then be repeated.

An alternate method to ensure co-planarity between the display and the captured slice may be based on parallax. This method preferably aligns targets in the tomographic image with the corresponding features in the virtual image from one point of view, and then move the video camera to another point of view to verify continued alignment. Errors thus introduced in the alignment could be used to calculate corrections in the position of the flat panel monitor, bringing its virtual image into co-planarity with the ultrasound slice.

The parallax method could be used on the "virtual line of sight" phantom (with tubes containing LED's, FIG. 9) by providing multiple tubes for each target pointing in different directions. For example, a system of three targets with six tubes may be used as an exemplary embodiment, with each set of three tubes converging on a different viewing location. Video cameras at these two locations would capture the required parallax information.

The present invention may also take advantage of methods and apparatuses for the guiding of invasive devices such as guiding the insertion of a needle 1000 during a biopsy procedure. One preferred embodiment, shown in FIG. 10, introduces the use of an oriented light source 1005 to specify a path to an internal target A. For example, in addition to the flat panel display 1010 (or in place of the flat panel display), a tube containing a light source 1015 (or simply a directional light source such as a laser) is positioned on the same side of the mirror as the viewer such that the virtual image of the light 1020 coincides with the desired needle path 1000 within the patient. The combined view of the two image paths is depicted as image line 1025. The intended needle path 1000 may be determined in a number of ways, including the use of image data from a scanner physically attached to the device or otherwise geometrically related to the device by use of a jig if image data was previously acquired.

The laser or other light may also be reflected off of the flat panel display and up to the half-silvered mirror. With this orientation, the light source 1015 would not interfere with the reflection of the displayed tomographic slice, and the user's view 1025 may be less obstructed. An almost limitless configuration of light sources and mirrors could be used to effect this reflection.

Figure 10:
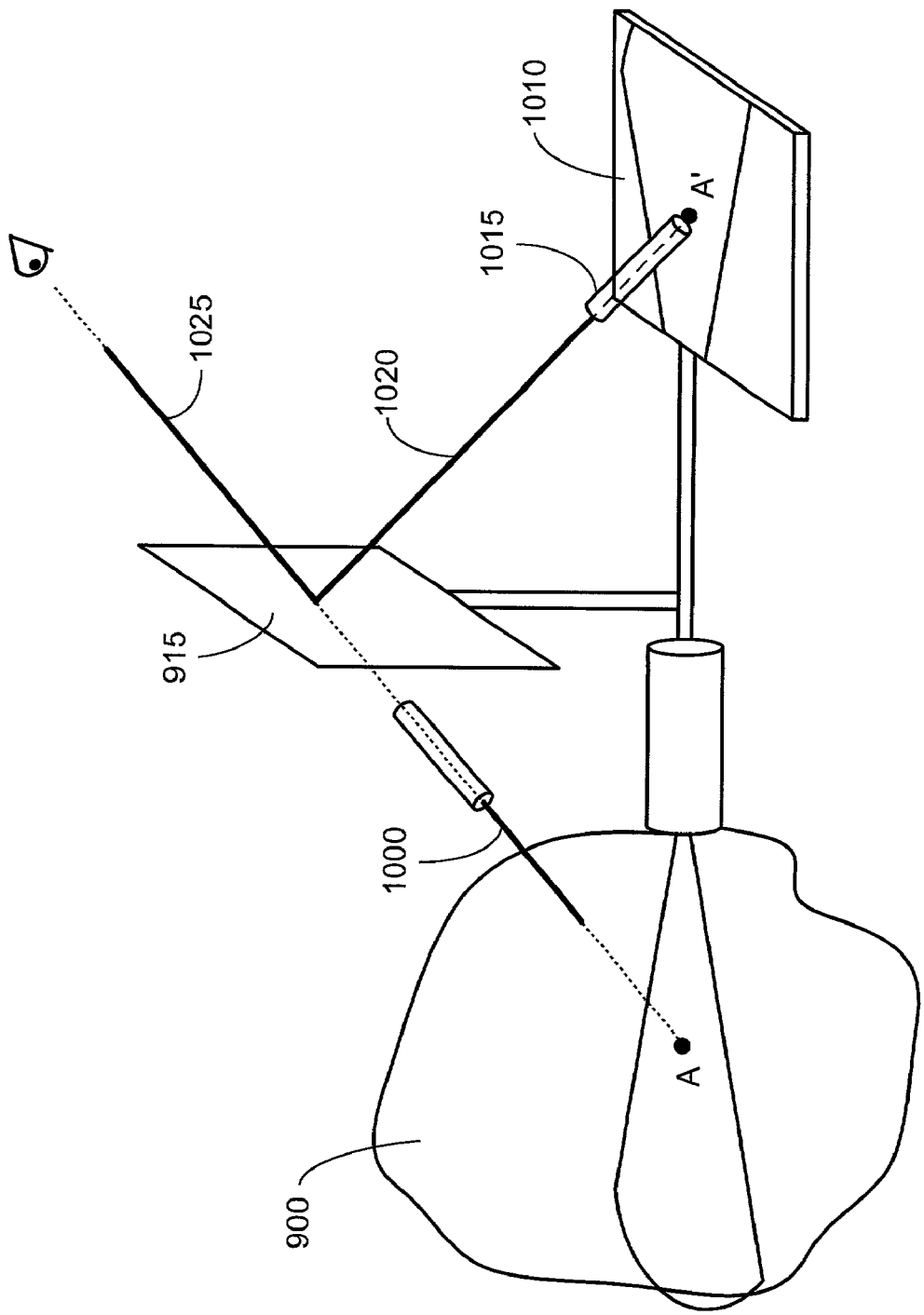
FIG. 10 shows a light source guidance method according to the present invention.

To determine light source placement, human and/or computer analysis of the image data (which may be 3D in the case of CT, MRI, 3D ultrasound, etc.) may be used to initially and/or continually provide a needle path that hits the target while avoiding critical structures such as arteries. Light emanates from the tube such that the operator may find the appropriate entrance location and initial orientation for the needle. During insertion, continual guidance may be intuitively applied by keeping the exposed shaft of the needle aligned with the virtual image of the tube. Marks on the needle shaft can be visually aligned with corresponding marks on the tube to determine depth of insertion and alert the operator when the target has been reached. FIG. 10 shows a 2D version of this embodiment.

The reverse of this "light" system could also be used to guide needles or other tools into the target object. For example, a biopsy needle (or other tool) with small lasers mounted on the back of, and on opposite sides of, the needle which point parallel to the long axis of the needle (down its shaft) may be used. The lasers will be reflected off of the half silvered-mirror and down to the face of the flat panel display (with the half-silvered mirror oriented parallel to the plane of the display and the image capture device). These lasers will appear as two "dots" (or other shapes) on either side of the target on the flat panel display. These marking dots represent the position at which the needle is currently aimed in the target image. By watching the movement of the dots on the face of the display (or in the reflection inside the patient), the needle or other tool may be properly guided into the target image.

One potential drawback of at least one embodiment of the present invention is the angle of refraction that occurs as the various images pass through the glass of the half-silvered mirror. Because the reflected image bounces off the face of the mirror and the direct view of the target object passes through the glass of the mirror, there will be a refractive offset (error) between the two images due to the thickness of the glass.

Figure 11:
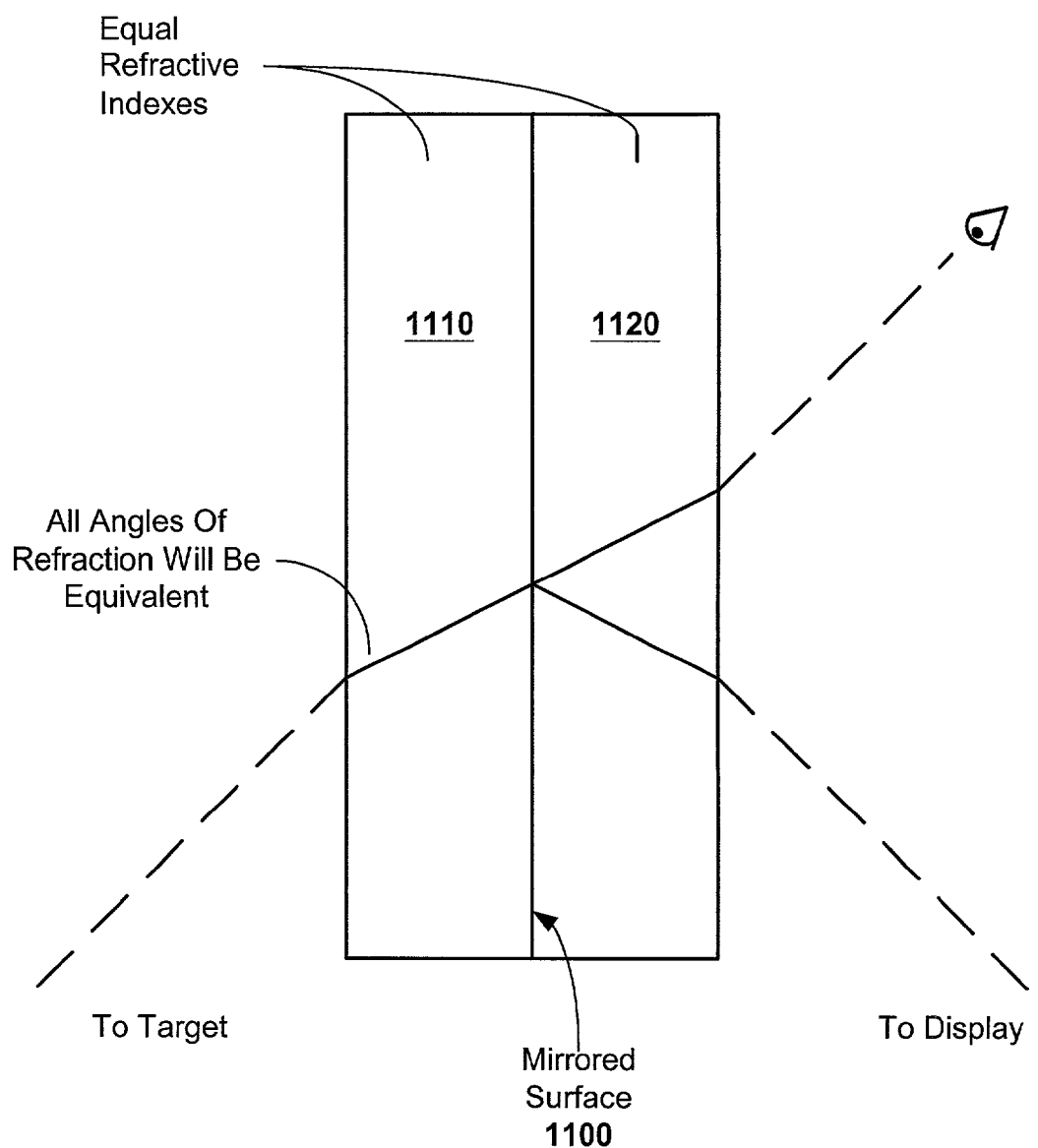
FIG. 11 details a reflective surface embedded between two surfaces with equivalent refractive properties.

FIG. 11 shows one exemplary apparatus for addressing this potential limitation. In FIG. 11, a cross-section of the mirrored surface 1100 of the half-silvered mirror is shown between two equal thickness pieces of glass 1110, 1120 (with the same refractive index). With this structure, both the direct view and the reflected image will pass through the glass 1110, 1120 and be refracted an equivalent amount. In other words, the same error due to refraction will be imparted to each of the image lines. This orientation will therefore preferably correct for the problems of refraction in the half-silvered mirror.

Figure 12:
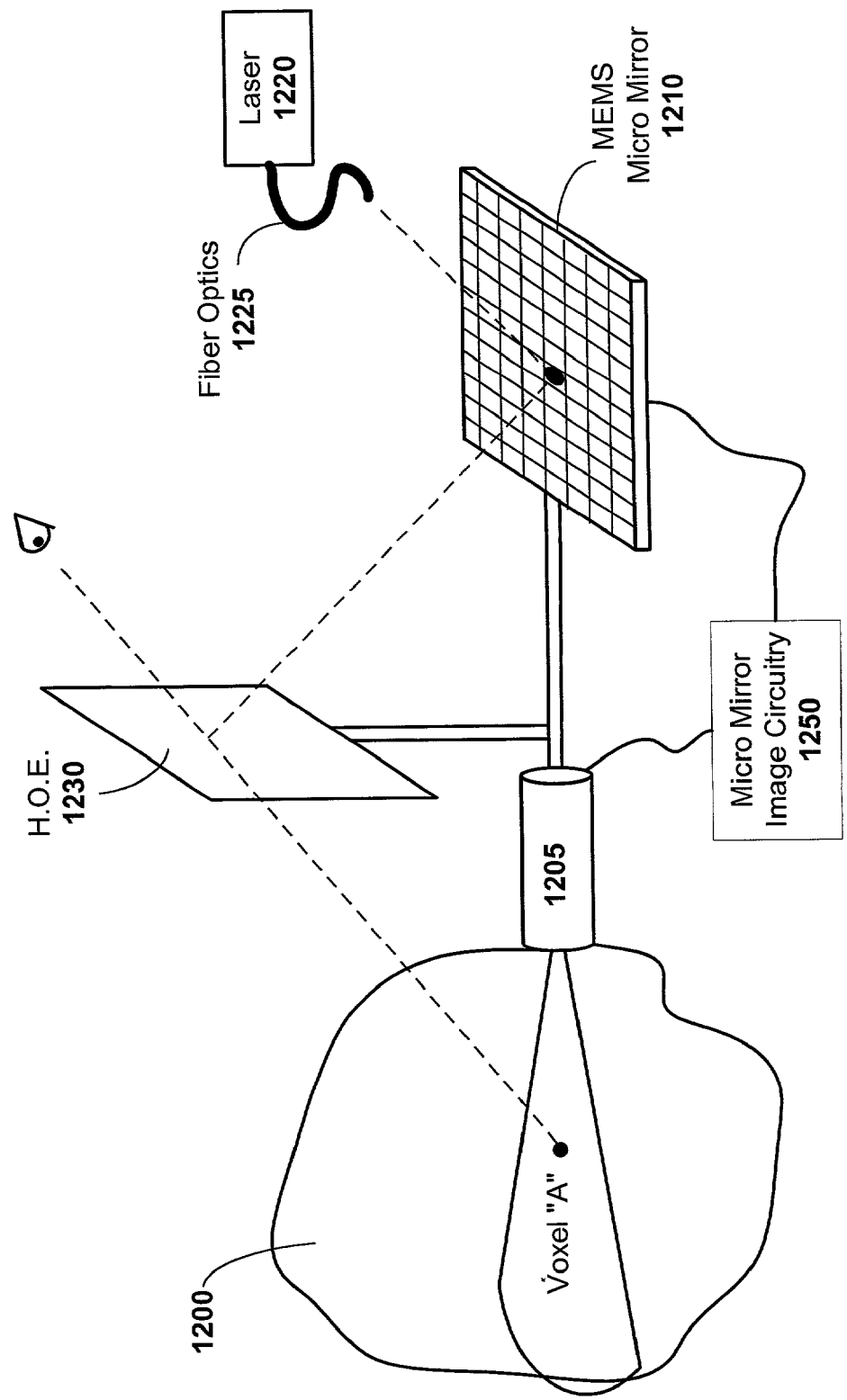
FIG. 12 shows an embodiment of the present invention with a holographic plate.

The half-silvered mirror embodiments of the present invention (described above) could also be altered to use a Holographic Optical Element (HOE) instead of the mirror. This is just another example of the generalized "partially reflective, partially transparent, surface." For example, FIG. 12 shows one presently preferred embodiment of the present invention including an ultrasound transducer 1205 with an HOE or "holographic plate" 1230 and a micro-mirror MEMS chip 1210 mounted thereon. An HOE 1230 is the hologram of an optical system that serves the same function normally performed by mirrors and lenses. The micro-mirror MEMS chip 1210 preferably contains a large array of individual micro-mirrors, for example in a grid pattern as shown in FIG. 12.

This system works by reflecting laser light 1220 off of each of the micro-mirrors that make up the micro-mirror device 1210. The captured tomographic slice image is used to control (via circuitry 1250) each of the tiny micro-mirrors 1210 to determine whether or not the laser light 1220 is reflected up the HOE 1230. Specifically, the output of a laser 1220 may be routed via a fiber optic cable 1225 to the micro-mirror chip 1210 so that coherent light may be reflected onto the HOE 1230 by any given micro-mirror when that particular micro-mirror is activated. This activation is determined by a given pixel in a video signal from the ultrasound transducer which represents a voxel (A) in the ultrasound slice.

The video image from the image capture device 1205 (e.g., ultrasound scanner) may be appropriately scaled, rotated, translated and cropped (via circuitry 1250) to occupy the array of micro-mirrors on the chip 1210. The HOE 1230 is preferably designed so that light reflected by a given micro-mirror appears to emanate from a particular location within the target, namely, the location of the voxel (A) in the tomographic scan corresponding to that particular pixel in the ultrasound image. Thus, the ultrasound slice as a whole appears to emanate in real-time from within the target object 1200 at its actual location.

Although FIG. 12 shows the major components of such a holographic system, parts of the optical system (mirrors and/or lenses) required to direct the laser light 1220 onto the micro-mirror chip 1210 and the phase modulation system used to reduce speckle normally resulting from coherent light are not shown for clarity. These and other desired components of a laser light system are well known to one skilled in the art. Additionally, FIG. 12 depicts only the particular case involving an ultrasound scanner capturing a single tomographic slice. Other tomographic imaging modalities, including those that operate in 3D (described above), may also be displayed using this method, since the 2D array of micro-mirrors can be mapped into a 3D space within the patient.

The holographic system establishes the geometric relationship between the micro-mirrors and the virtual tomographic image. The content of the image is established by the video signal from the ultrasound scanner, whose pixels control to the individual elements of the micro-mirror device. It is further noted that the HOE embodies a transform function for creating a magnified view-independent virtual image that could be created using lenses and mirrors, whereas non holographic optical elements would be very large and somewhat less desirable.

Figure 13:
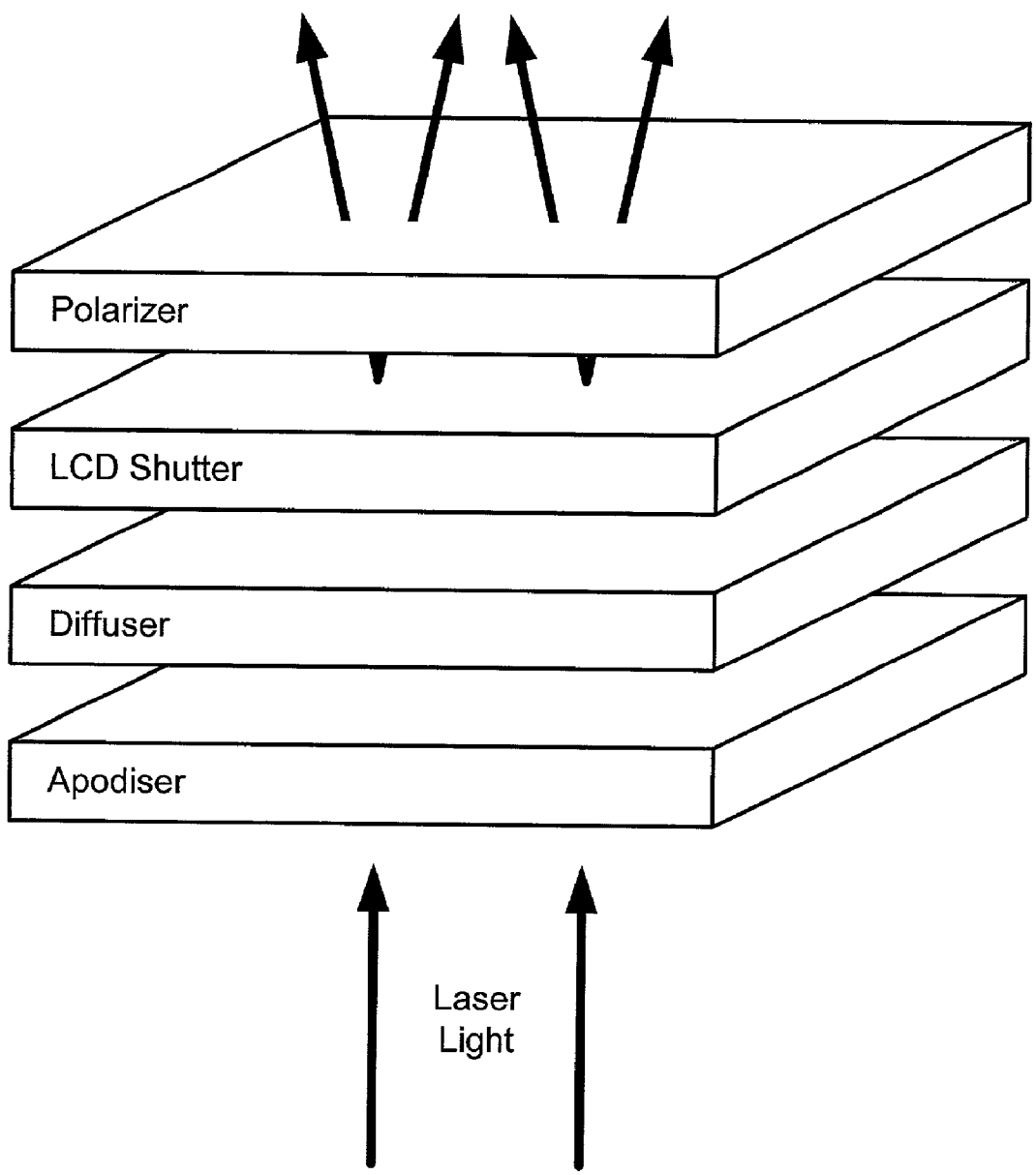
FIG. 13 shows exemplary material layers combined in an LCD.

Difficulties may arise with the use of the micro-mirror device due to the small angle of deflection capable in the micro-mirrors. Therefore, other devices could be used in place of the MEMS device such as a Liquid Crystal Display (LCD) or any device capable of switching on/off individual localized sources of monochromatic light directed at the HOE 1230. For example, FIG. 13 shows an exemplary LCD shutter with laser light (attempting) to pass through the shutter towards the HOE. In FIG. 13, the directional laser light passes through the non-polarizing apodiser and diffuser. The LCD shutter and the polarization layer work in tandem to determine the amount of light that passes through each LCD shutter based on the relative polarization of these two layers.

Each LCD shutter can be quickly turned on/off so as to direct the ultrasound image up to the HOE. In much the same was as with the MEMS device, each individual LCD shutter may correspond to a pixel in the captured tomographic slice and will be turned on/off based on whether that pixel currently exists in the image. With sufficiently fast switching, the same result on the face of the HOE is achieved.

A simplified version of the HOE could also be used in the present invention as depicted in FIG. 14. For example, it is known in general optics that the hologram of an ideal mirror is simply a grating. The hologram of a simple convex lens is a zone-plate, i.e., a series of concentric rings that create an interference pattern.

The hologram pattern can be calculated using the lens equation: $1/x+1/y=1/f$ (where x=distance from lens on one side; y=distance from lens on the other side; and f=focal length). A series of correspondence points thus exists on opposite sides of the lens which can be used to project the array of emission points (from the MEMS micro mirrors or LCD device) to the corresponding virtual locations in the ultrasound slice. In other words, a single hologram can map the whole image, rather than a separate hologram for each pixel. The same approach could be used to map from the MEMS (or LCD) device mounted parallel to the HOE to a "C-mode" slice from a 3D ultrasound machine, as described earlier and shown in FIG. 3.

The hologram of a tomographic slice, therefore, would generally be an off-axis sector of this zone plate as shown in FIG. 14. The partial spherical etches in the HOE will produce spherical wavefronts from A',B',C' when illuminated at A,B,C with coherent light, because the zone plate acts as a lens. FIG. 14B shows a side view of the device. However, the hologram will have some "keystone-shaped" distortions as shown in FIG. 14. These distortions can be compensated for by a corresponding distortion of the image sent to the MEMS or LCD device (from circuitry 1250). There may also be problems with resolution in parts of the image due to inefficient use of the entire MEMS or LCD device. The 3D ultrasound version might also experience distortion or curvature in the "C-mode" slice, and these may be corrected by judicious selection of the particular voxels to be displayed.

The resulting HOE is a much simpler 2D HOE that could be implemented as a "surface plate" rather than the HOE described above that would likely require a "volume plate".

The surface plate is easier to manufacture and may be much cheaper to produce. The present HOE may be manufactured by etching the calculated pattern into a chromium coated glass plate.

The present invention may also be used to display multiple tomographic slices simultaneously. For example, this can be accomplished using the mirror orientation described in several embodiments above with the addition of multiple flat panel displays. If each of the flat panel displays was oriented with respect to the viewer-side face of the half-silvered mirror (according to the calibration methodologies described above), then multiple tomographic slices could be superimposed on the direct view of the target object on the face of the half-silvered mirror. This may give the impression of seeing an internal 3D view of the target object. However, because all of the various images are reflected to a flat surface, the resulting combined image may be difficult to comprehend in certain circumstances.

Alternatively, multiple MEMS micro-mirror devices or multiple LCD shutters could be used to simultaneously display multiple captured slice images in real-time on the HOE. In the same way as multiple flat panel displays may be used with the half-silvered mirror embodiments, two or more micro-mirror devices or LCD shutters could be oriented such that they direct laser light to the HOE to simultaneously show multiple tomographic slice images on the HOE. Alternatively, by dividing a single MEMS into several sections, each with a different holographic transform, multiple slices could appear to be displayed on the HOE simultaneously. However, crosstalk between the slices may be easier to minimize if each image is displayed on its own MEMS chip, rather than sharing sections of a single MEMS chip. The HOE device also has the advantage over the mirror that a slice displayed roughly "edge-on" could be viewed from either side by moving the viewpoint. This multiple-device orientation may reduce alignment problems related to showing multiple slices on one device, but it may also increase the cost of the system. Therefore, different orientations of these components will be preferred for different applications.

Nothing in the above description is meant to limit the present invention to any specific materials, geometry, or orientation of elements. Many part/orientation substitutions are contemplated within the scope of the present invention and will be apparent to those skilled in the art. The embodiments described herein were presented by way of example only and should not be used to limit the scope of the invention.

Although the invention has been described in terms of particular embodiments in an application, one of ordinary skill in the art, in light of the teachings herein, can generate additional embodiments and modifications without departing from the spirit of, or exceeding the scope of, the claimed invention. Accordingly, it is understood that the drawings and the descriptions herein are proffered only to facilitate comprehension of the invention and should not be construed to limit the scope thereof.

What is claimed is:

1. An imaging device comprised of:
    a removable image capture device for capturing an image of the internal structure of a target object;
    a removable display assembly including a display for displaying a captured image from the image capture device and a partially reflective surface oriented to reflect the captured image to an operator of the imaging device, such that the reflected captured image forms a virtual image that is geometrically superimposed with said internal structure being imaged and is merged with a direct view of the target object independent of the viewing location of the operator.

2. The imaging device of claim 1, further comprising:
    a jig, wherein said image capture device and said display assembly are removable from said jig such that said jig retains a predetermined geometry between the image capture device and the display assembly even when the image capture device and the display assembly are not present at the same time.

3. The imaging device of claim 2, wherein said image capture device captures a two dimensional image.

4. The imaging device of claim 2, wherein said image capture device captures a three dimensional data set.

5. The imaging device of claim 2, wherein said display is a flat panel display.

6. A method for viewing a target object, comprising the steps of:
    inserting an image capture device assembly into a jig;
    capturing a tomographic image of a target object;
    removing said image capture device assembly from said jig;
    inserting a display assembly, including a display and a partially reflective surface into said jig;
    reflecting said displayed tomographic image onto said partially reflective surface such that an operator can directly view the target object through said partially reflective surface merged with the tomographic image reflected by the partially reflective surface thereby forming a virtual image that is geometrically superimposed with said tomographic image, wherein said merger is independent of operator viewing location.

7. The method of claim 6 further including the step of:
    keeping the target object substantially motionless between the time of capturing the image and reflecting the image onto the partially reflective surface.

8. An imaging device calibration system, comprising:
    a phantom target object;
    an image capture device for capturing an image of the internal structure of the target object;
    a display for displaying a captured image from the image capture device; and
    a partially reflective surface oriented to reflect the captured image to an operator of the imaging device, such that the reflected captured image forms a virtual image and is merged with a direct view of the target object independent of the viewing location of the operator, wherein said phantom target object includes at least three target beads embedded therein.

9. The imaging device calibration system of claim 8, wherein at least three of said at least three beads are arranged in an approximate equilateral triangle in the plane of the image captured by the image capture device.

10. The imaging device calibration system of claim 8, wherein said phantom target further comprises a plurality of tubes mounted on an outer surface of the phantom target object, wherein a long axis of each of said tubes is directed along an operator's line of sight to each of said target beads.

11. The imaging device calibration system of claim 10, wherein each of said tubes further comprises an LED.

12. The imaging device calibration system of claim 8, further comprising a computer capable of calculating an affine transform between a stored location of each of the target beads and an operator's line of sight view of each of the target beads as seen through the partially reflective surface.

13. The imaging device of claim 12, wherein said phantom target object is filled with a gel.

14. A method for calibrating an imaging device including an image capture device, a display, and a partially reflective surface, comprising the steps of:
  suspending at least three target beads in a phantom target object filled with gel;
  affixing a hollow tube to the outside of said phantom target object for each target bead, said tube being oriented such that an operator has a direct line of sight through the partially reflective surface, through the tube to its respective target bead within the phantom target object;
  capturing a tomographic image of the target beads with the image capture device;
  displaying the captured image on the display such that the image is reflected by the mirror partially reflective surface to form a virtual image that is geometrically superimposed with a direct view of said phantom target object; and
  calculating an affine transform between a stored location of each of the target beads and an operator's line of sight view of each of the target beads as seen through the partially reflective surface to geometrically superimpose the virtual image with corresponding underlying structures in said phantom target object.

15. The method for calibrating an image capture device of claim 14, further comprising the step of:
  inserting an LED into each of said tubes affixed to the outer surface of the phantom target object to provide a visual indication of target bead location within the phantom target.

16. The method for calibrating an imaging device of claim 15, further comprising the step of:
  removing the gel from the phantom target before said step of displaying the captured image.

17. The method for calibrating an imaging device of claim 14, further comprising the step of:
  establishing the geometric co-planarity of the virtual image of the display and the slice captured by the image capture device.

18. The method for calibrating an imaging device of claim 14, wherein said step of establishing co-planarity is accomplished using a plane of focus technique with a video camera.

19. The method for calibrating an imaging device of claim 14, wherein said step of establishing co-planarity is accomplished using a parallax method with a video camera.

20. An imaging device comprised of:
  an image capture device for capturing an image of the internal structure of a target object;
  a display for displaying a captured image from the image capture device;
  a partially reflective surface oriented to reflect the captured image to an operator of the imaging device, such that the reflected captured image forms a virtual image that is geometrically superimposed with said internal structure being imaged and is merged with a direct view of the target object independent of the viewing location of the operator; and
  a directional light source oriented such that light from the source is reflected off of the partially reflective surface and up to operator.

21. The imaging device of claim 20, wherein said directional light source is mounted on the face of the display.

22. The imaging device of claim 20, wherein said directional light source is mounted such that light from the source is reflected off of the display and up to the partially reflective surface.

23. The imaging device of claim 20, wherein said directional light source is a laser.

24. An imaging device comprised of:
  an image capture device for capturing an image of the internal structure of a target object;
  a display for displaying a captured image from the image capture device;
  a partially reflective surface oriented to reflect the captured image to an operator of the image capture device, such that the reflected captured image forms a virtual image that is geometrically superimposed with said internal structure being imaged and is merged with a direct view of the target object independent of the viewing location of the operator; and
  a plurality of directional light sources attached adjacent and parallel to the long axis of a surgical tool and oriented such that light from at least one of said plurality of directional light sources is reflected off of the partially reflective surface and onto the display.

25. The imaging device of claim 24, wherein said plurality of light sources is two light sources, and said two light sources make two indicator dots on the face of the display on opposite sides of a location in the target object to which the surgical tool is currently directed.

26. The imaging device of claim 25, wherein said surgical tool further includes depth of insertion indicator markings.

27. An imaging device comprised of:
  an image capture device for capturing an image of the internal structure of a target object;
  a display for displaying a captured image from the image capture device; and
  a partially reflective surface oriented to reflect the captured image to an operator of the imaging device, such that the reflected captured image forms a virtual image that is geometrically superimposed with said internal structure being imaged and is merged with a direct view of the target object independent of the viewing location of the operator, wherein said partially reflective surface is disposed between two equal thicknesses of a transparent material with equivalent refractive properties.

28. The imaging device of claim 27, wherein said transparent materials are glass.

29. An imaging device comprised of:
  an image capture device for capturing an image of the internal structure of a target object;
  a holographic optical element;
  a directional light source;
  means for transmitting light from the light source to the holographic optical element, such that a virtual image of the captured image is merged with a direct view of the target object through the holographic optical element independent of the viewing location of the operator.

30. The imaging device of claim 29, wherein said means for transmitting light is a MEMS mirror array which reflects light to the holographic optical element.

31. The imaging device of claim 30, wherein said MEMS array is divided into a plurality of sections, each section adapted to reflect a different captured image to the holographic optical element.

32. The imaging device of claim 29, wherein said means for transmitting light is an LCD that either blocks or transmits light from the directional light source to the holographic optical elements.

33. The imaging device of claim 29, further comprising:
imaging circuitry connected to the image capture device and the means for transmitting light, wherein said circuitry transforms the captured image into a format which transmits the light to the holographic optical element to display the captured image.

34. The imaging device of claim 29, wherein said light source is a laser.

35. The imaging device of claim 29, wherein said image capture device is an ultrasound scanner.

36. The imaging device of claim 29, wherein said holographic optical element is a two dimensional surface plate holographic optical element.

37. The imaging device of claim 36, wherein said holographic optical element is etched in a pattern that is an off-axis series of concentric circles.

* * * * *

UNITED STATES PATENT AND TRADEMARK OFFICE
CERTIFICATE OF CORRECTION

Page 1 of 1

PATENT NO. : 7,559,895 B2
APPLICATION NO. : 10/126453
DATED : July 14, 2009
INVENTOR(S) : George DeWitt Stetten and Andreas G. Nowatzyk It is certified that error appears in the above-identified patent and that said Letters Patent is hereby corrected as shown below:

On the Title Page

Please replace Item 63 on the face of the above-referenced patent with the following paragraph.

"This application is a continuation-in-part of U.S. application no. 09/686,677 filed October 11, 2000 (now U.S. patent no. 6,599,247, issued July 29, 2003)."

Please replace the paragraph under "RELATED APPLICATION DATA" beginning on col. 1, line 6 of the above-referenced patent with the following paragraph.

"This application is a continuation-in-part of U.S. application no. 09/686,677 filed October 11, 2000 (now U.S. patent no. 6,599,247, issued July 29, 2003)."

Signed and Sealed this
Twenty-seventh Day of March, 2012

David J. Kappos
*Director of the United States Patent and Trademark Office*